(12) United States Patent
Hajitou et al.

(10) Patent No.: US 10,471,138 B2
(45) Date of Patent: Nov. 12, 2019

(54) BACTERIOPHAGE-POLYMER HYBRID

(71) Applicant: Imperial College Innovations Limited, London (GB)

(72) Inventors: Amin Hajitou, London (GB); Teerapong Yata, London (GB)

(73) Assignee: Imperial College Innovations Limited, London (GB)

( * ) Notice: Subject to any disclaimer, the term of this patent is extended or adjusted under 35 U.S.C. 154(b) by 0 days.

(21) Appl. No.: 16/135,540

(22) Filed: Sep. 19, 2018

(65) Prior Publication Data

US 2019/0083610 A1 Mar. 21, 2019

Related U.S. Application Data

(63) Continuation of application No. 14/889,823, filed as application No. PCT/GB2014/051447 on May 12, 2014, now abandoned.

(30) Foreign Application Priority Data

May 15, 2013 (GB) .................................. 1308745.7

(51) Int. Cl.
*A61K 39/385* (2006.01)
*A61K 35/76* (2015.01)
(Continued)

(52) U.S. Cl.
CPC ............ *A61K 39/385* (2013.01); *A61K 35/76* (2013.01); *A61K 47/543* (2017.08); *A61K 47/59* (2017.08); *A61K 47/61* (2017.08); *A61K 47/645* (2017.08); *A61K 47/6901* (2017.08); *A61K 47/6921* (2017.08); *C12N 15/86* (2013.01); *A61K 48/00* (2013.01); *A61K 2039/5256* (2013.01); *A61K 2039/55583* (2013.01); *C07K 2319/74* (2013.01); *C12N 2795/10043* (2013.01); *C12N 2795/10045* (2013.01)

(58) Field of Classification Search
None
See application file for complete search history.

(56) References Cited

U.S. PATENT DOCUMENTS

2004/0048243 A1  3/2004  Arap et al.
2005/0112550 A1  5/2005  Gershoni et al.
(Continued)

FOREIGN PATENT DOCUMENTS

WO  1999010014 A2  3/1999
WO  2002081635 A2  10/2002
(Continued)

OTHER PUBLICATIONS

PCT/GB2014/051446 International Search Report and Written Opinion dated Jul. 30, 2014; 17 pages.
(Continued)

*Primary Examiner* — Michelle S Horning
(74) *Attorney, Agent, or Firm* — Linda B. Huber; Nixon Peabody LLP

(57) ABSTRACT

The invention provides a targeted bacteriophage-polymer complex comprising a recombinant targeted-bacteriophage and a cationic polymer. The complex has a net positive charge. The invention provides methods of preparing bacteriophages and complexes thereof, and to their uses for the delivery of transgenes in a variety of gene therapy applications.

18 Claims, 39 Drawing Sheets

Figure 1A:
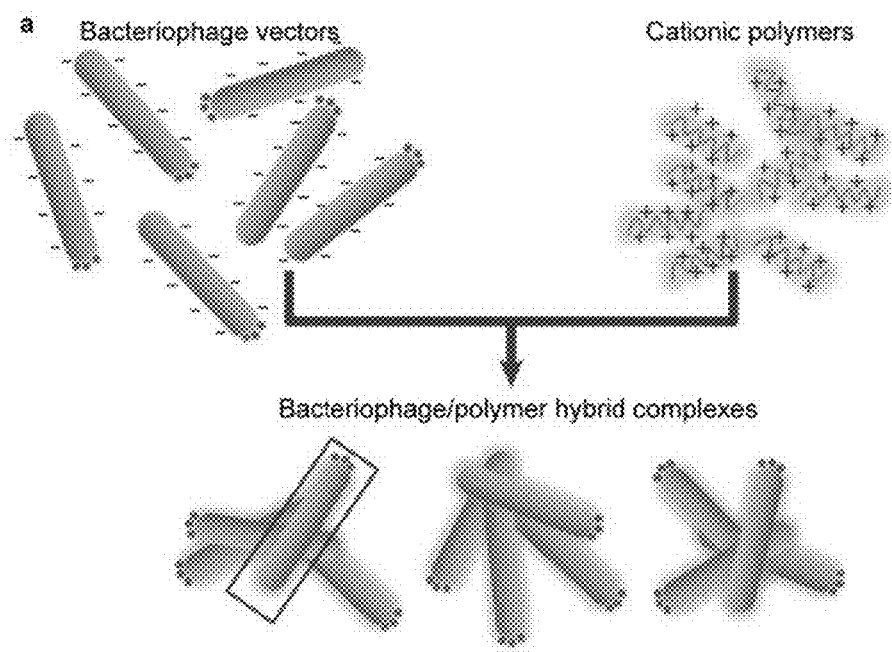

Specification includes a Sequence Listing.

(51) Int. Cl.
  C12N 15/86   (2006.01)
  A61K 47/54   (2017.01)
  A61K 47/59   (2017.01)
  A61K 47/61   (2017.01)
  A61K 47/64   (2017.01)
  A61K 47/69   (2017.01)
  A61K 48/00   (2006.01)
  A61K 39/00   (2006.01)

(56) References Cited

U.S. PATENT DOCUMENTS

2006/0105387 A1   5/2006   Prior et al.
2016/0114032 A1   4/2016   Hajitou et al.
2017/0340684 A1   11/2017  Hajitou et al.

FOREIGN PATENT DOCUMENTS

WO   2003/077953 A2   9/2003
WO   2006095345 A2   9/2006
WO   2009024591 A1   2/2009
WO   2014184528 A1   11/2014
WO   2014184529 A1   11/2014

OTHER PUBLICATIONS

PCT/GB2014/051447 International Search Report and Written Opinion dated Sep. 3, 2014; 14 pages.
Chung et al. Fabrication of engineered M13 bacteriophages into liquid crystalline films and fibers for directional growth and encapsulation of fibroblasts. Soft Matter (2010). 6(18): 4454-4456.
Groot-Wassink, T. Quantitative Imaging of Na/I Symporter Transgene Expression Using Positron Emission Tomography in the Living Animal. Molecular Therapy (2004). 9(3):436-442.
Guo et al. Construction of bifunctional phage display for biological analysis and immunoassay. Anal Biochem (2010). 396(1):155-157.
Hirosue et al. pH-Dependent lytic peptides discovered by phage display. Biochemistry (2006). 45(20):6476-6487.
Kia et al. Dual Systemic Tumor Targeting with Ligand-Directed Phage and Grp78 Promoter Induces Tumor Regression. Molecular Cancer Therapeutics (2012). 11(12):2566-2577.
Larocca et al. Targeting Bacteriophage to Mammalian Cell Surface Receptors for Gene Delivery. Human Gene Therapy (1998). 9:2393-2399.
Prisco et al. Filamentous Bacteriophage Fd as an Antigen Delivery System in Vaccination. International Journal of Molecular Sciences (2012). 13(12):5179-5194.
Rangel et al. Combinatorial targeting and discovery of ligand-receptors in organelles of mammalian cells. Nat Commun (2012). 3:788, 10 pages.
Sartorius et al. Vaccination with filamentous bacteriophages targeting DEC-205 induces DC maturation and potent anti-tumor T-cell responses in the absence of adjuvants. Eur J Immunol (2011). 41:2573-2584.
Scott et al. Searching for Peptide Ligands with an Epitope Library. Science (1990). 249:386-390.
Scott et al. EBI Accession No. EMBL: AAF78530. Filamentous phage display vector f88-4 recombinant major coat protein precursor. (2000). 1 pages.
Van Houten et al. Filamentous phage as an immunogenic carrier to elicit focused antibody responses against a synthetic peptide. Vaccine (2006). 24(19):4188-4200.
Akuta et al., Enhancement of Phage-Mediated Gene Transfer by Nuclear Localization Signal, 2002, Biochem. Biophys. Res. Commun., vol. 297(4): pp. 779-786.
Attwood, T., The Babel of Bioinformatics, 2000, Science, vol. 290(5491), pp. 471-473.
Ashley et al., Cell-Specific Delivery of Diverse Cargos by Bacteriophage MS2 Virus-Like Particles, 2011, ACS Nano, vol. 5(7), pp. 5729-5745.
Baker et al., Protein Structure Predication and Structural Genomics, 2001, Science, vol. 294(5540), pp. 93-96.
Genbank: AF218363 Filamentous Phage Display Ventor f88-4, 2000.
Genbank: AF218364 Filamentous Phage Display Ventor fUSE5, 2000.
Lamboy et al., Chemical and Genetic Wrappers for Improved Phage and RNA Display, 2008, Chembiochem., vol. 9 (17), pp. 2846-2852.
Hajitou et al. A hybrid vector for ligand-directed tumor targeting and molecular imaging. Cell (2006). 125(2):385-98.
Greenstein et al. Indroduction to vectors derived from filamentous phages. Curr Protoc Mol Biol (2001). Ch. 1: Unit 1.14, p. 15.
Aujame et al., Experimental Design Optimization of Filamentous Phage Transfection into Mammalian Cells by Cationic Lipids, BioTechniques, 2000, vol. 28, pp. 1202-1213.
Chen et al., Cancer Gene Therapy by Direct Tumor Injections of a Nonviral T7 Vector Encoding a Thymidine Kinase Gene, Human Gene Therapy, 1998, vol. 9, pp. 729-736.
Ishiura et al., Phage Particle-Mediated Gene Transfer to Cultured Mammalian Cells, Molecular and Cellular Biology, 1982, vol. 2(6), pp. 607-616.
Lamboy et al., Phage Wrapping with Cationic Polymers Eliminates Non-Specific Binding between M13 Phage and High pI Target Proteins, J Am Chem Soc., 2009, vol. 131(45), pp. 16454-16460.
Sidhu et al., Phage Display in Phamaceutical Biotechnology, Current Opinion in Biotechnology, 2000, vol. 11, pp. 610-616.
Zecchin et al., Transfection and DNA-Mediated Gene Transfer, Methods of Molecular Biology, 2011, vol. 731, pp. 435-450.

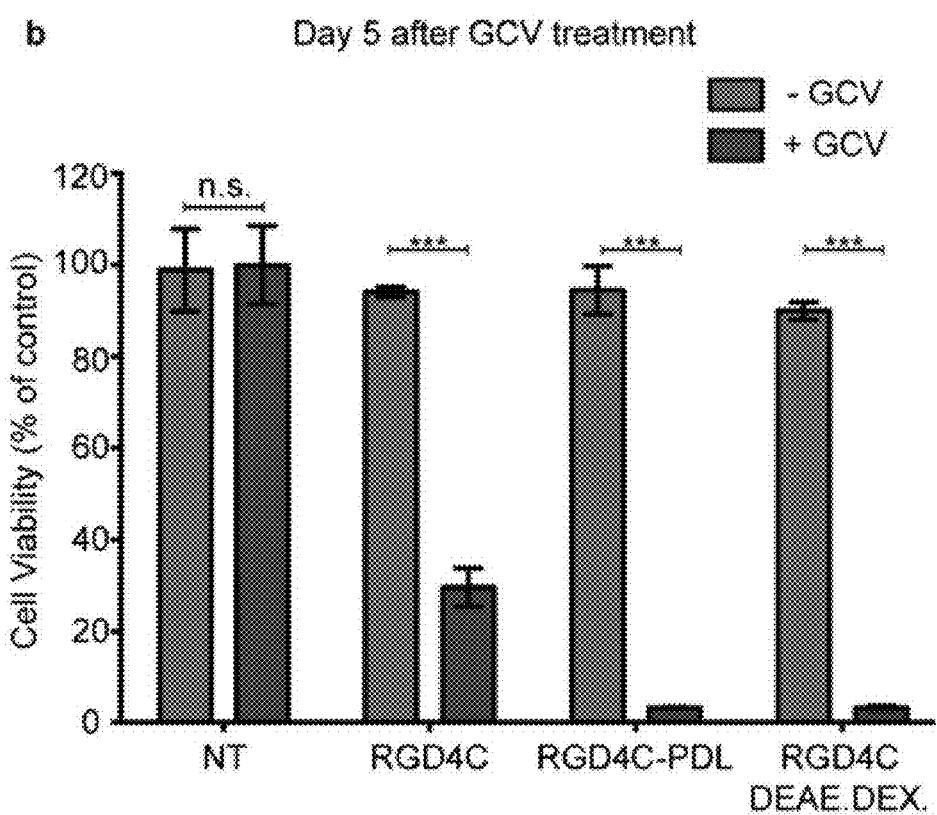

SEQUENCE LISTING

```
<160> NUMBER OF SEQ ID NOS: 1

<210> SEQ ID NO 1
<211> LENGTH: 9
<212> TYPE: PRT
<213> ORGANISM: Artificial Sequence
<220> FEATURE:
<223> OTHER INFORMATION: synthetic peptide

<400> SEQUENCE: 1

Cys Asp Cys Arg Gly Asp Cys Phe Cys
1               5
```

BACTERIOPHAGE-POLYMER HYBRID

This application is a continuation of U.S. patent application Ser. No. 14/889,823 filed Nov. 6, 2015, which is the National Phase of International Application No. PCT/GB2014/051447, filed May 12, 2014, which designated the U.S. and that International Application was published under PCT Article 21(2) in English. This application also includes a claim of priority under 35 U.S.C. § 119(a) and § 365(b) to British patent application No. GB 1308745.7 filed May 15, 2013, now expired, the entirety of which is hereby incorporated by reference.

The present invention relates to bacteriophages, and particularly to novel bacteriophage complexes. The invention extends to methods of preparing bacteriophages and complexes thereof, and to their uses for the delivery of transgenes in a variety of gene therapy applications.

The successful delivery of transgenes to desired target sites in vivo following systemic administration would have a major impact on the practice of medicine, in particular on the advance of gene therapy, genetic imaging and DNA vaccine applications. Moreover, targeting systemic gene delivery to diseased tissue presents an efficient and safer approach to "theragnostics", i.e. both gene therapy and genetic imaging combined into a single vector system. Most progress in gene delivery to date has been achieved using eukaryotic viruses, such as Adenovirus, Adeno-associated virus (AAV) and Lentivirus, which provide superior gene delivery vectors. However, systemic administration using these eukaryotic viruses has had limited success due to their undesired uptake by the liver and reticulo-endothelial system, insertional mutagenesis, immunogenicity resulting from reactions with the complement or pre-existing antibodies, and broad tropism for mammalian tissues.

Bacteriophages (i.e. bacterial viruses), have attracted attention as safe vectors for targeted systemic delivery of transgenes, as they do not have an intrinsic tropism for mammalian cell receptors, but can be modified to display tissue-specific ligands on their coat proteins without disruption of their virus structure. Such vectors have many advantages over animal viral vectors and existing gene delivery systems due to a number of promising characteristics. For example, bacteriophages are nanosized natural systems that are capable of efficiently condensing and packaging DNA. The high tolerance for phage coat protein mutations permits the insertion of foreign peptides into their capsid coats so that they can target desired cell types without the elimination of native tropism for bacteria. In addition, bacteriophages are safe, having long been used both prophylactically and for the treatment of bacterial infections, both in adults and children, with no safety concerns being identified. They have also been approved by the Food and Drug Administration (US-FDA) to be used as safe antibacterial food additives. The large-scale production and purification of phage vectors is simple and economical. Finally, they have a large capacity for insertion of foreign DNA.

Recently, the inventors introduced an improved version of a M13 phage-based vector, which incorporated a mammalian transgene cassette flanked by inverted terminal repeats (ITRs) from Adeno-associated virus 2 (AAV2) into the bacteriophage genome at a compatible location. This vector showed superior gene delivery compared to a regular phage vector with long-term gene expression in vivo following systemic administration. To demonstrate the efficacy of this improved phage in vivo, a phage displaying the cyclic RGD4C (CDCRGDCFC (SEQ ID NO:1)) peptide ligand was used to target overexpressed a, integrin receptors found in tumors. A recent study carried out under the direction of the National Cancer Institute of the USA has elegantly confirmed the potential of such phage technology. Targeted RGD4C-phage was used to deliver a cytokine, tumour necrosis factor-α (TNFα), to cancers diagnosed in pet dogs. Repeated doses proved safe and resulted in efficient expression of TNFα in the targeted tumours, leading to complete eradication of aggressive tumors in some individuals. Accordingly, bacteriophages are the first system that has been experimentally shown to offer safe and efficient delivery of transgenes to target tissues after systemic administration in vivo.

However, unfortunately, phage particles are comparatively poor vectors as they have evolved to infect only bacteria and, unlike eukaryotic viruses, bacteriophages have no intrinsic strategies for delivering genes to mammalian cells. As a result, because of this inherent limitation, phage-derived vectors need to be improved if they are going to find wide clinical application. There is therefore a need to provide an improved gene delivery system, which efficiently and specifically delivers transgenes to cells of interest in vivo.

The inventors have developed a novel hybrid vector system consisting of cationic polymers and a bacteriophage (e.g. M13), which has been genetically engineered to display a tumor-targeting ligand, and to carry a transgene cassette.

Hence, in a first aspect, there is provided a targeted bacteriophage-polymer complex comprising a recombinant targeted-bacteriophage and a cationic polymer, wherein the complex has a net positive charge.

As discussed in the Examples, the inventors have surprisingly demonstrated that incubating a recombinant bacteriophage with a cationic polymer results in the formation of a novel targeted bacteriophage-polymer complex (or "hybrid") having a net positive charge under physiological pH, which significantly and unexpectedly, enhances the ability of the bacteriophage to perform target-specific cellular transduction, for example when administered systemically. Therefore, the bacteriophage-polymer complex of the invention provides a novel hybrid vector platform, for use in a wide range of gene therapy applications, for example in cancer therapy.

It will be appreciated that bacteriophages are viruses (i.e. phages) that infect and replicate within bacteria. The advantage of using bacteriophages as gene delivery vectors, as opposed to other regular viruses, is that they do not naturally infect non-bacterial cells, such as mammalian cells, unless they are genetically modified to specifically do so.

Hence, the recombinant bacteriophage in the complex according to the invention may be genetically modified to comprise a nucleic acid sequence, which encodes a protein ligand that is capable of being expressed in the capsid coat, and which is also specific for a protein (e.g. a receptor) expressed on a target cell/tissue, so as to enable targeted delivery thereto. For example, in embodiments where the bacteriophage-polymer complex is used to treat cancer, the ligand may be a tumour-targeting ligand. By way of example, in one embodiment, the ligand may comprise the RGD4C ligand (see the Examples), which will be known to the skilled person. It will be appreciated that a phage displaying the cyclic RGD4C (CDCRGDCFC (SEQ ID NO:1)) peptide ligand targets overexpressed av integrin receptors found in tumours.

The same or an additional nucleic acid sequence may also encode a protein that produces a biological and preferably therapeutic effect on target cells transduced with the recombinant bacteriophage-polymer complex according to the invention. Hence, the bacteriophage may comprise a transgene, for example encoding the Herpes simplex virus tyrosine kinase gene (see Example 5), which may subsequently exert a biological or therapeutic effect on the target cell. Recombinant bacteriophages may include a variety of other functional elements in addition to the promoter, and the coding sequence encoding protein responsible for producing the therapeutic effect. Alternatively, the recombinant phage may be designed such that it integrates into the genome of a host cell. In this case, DNA sequences, which favour targeted integration (e.g. by homologous recombination) are envisaged.

The bacteriophage may be used as a recombinant vector for the delivery of the desired nucleic acid (e.g. a transgene) to a tissue specific target, irrespective of whether the vector is administered systemically or locally to a subject in vivo, applied to a mixture of cells in vitro, or applied to an organ ex vivo. In one embodiment of the invention, the nucleic acid may be DNA, which may be genomic DNA or cDNA. In another embodiment, the nucleic acid may be RNA, such as antisense RNA or shRNA.

Examples of bacteriophage, which may be used to produce the complex, include any negatively charged bacteriophage, preferably a filamentous phage, such as F1, Fd or M13. A preferred bacteriophage according to the invention is M13. In one embodiment, the bacteriophage preferably comprises a recombinant genome cassette carrying a transgene. Most preferably, M13 comprises a recombinant Adeno-associated virus (AAV) genome cassette carrying the transgene.

Preferably, the cationic polymer is any polymeric compound having a net positive charge at physiological pH. For example, the polymer may comprise a plurality of positively charged repeating units. The cationic polymer may be selected from a group consisting of: chitosan; poly-D-lysine (PDL); diethylaminoethyl (DEAE); diethylaminoethyl-dextran (DEAE.DEX); polyethyleneimine (PEI); polybrene; protamine sulphate; and a cationic lipid. For example, the cationic lipid may be selected from the group consisting of FUGENE® transfection reagent, LIPOFECTAMINE™ transfection reagent, and DOTAP (N-[1-(2,3-Dioleoyloxy)propyl]-N,N,N-trimethylammonium methyl-sulfate).

Preferably, the molecular weight of the cationic polymer is at least 4 kD, 6 kD, 10 kD, 50 kD, 100 kD or 500 kD. For example, the molecular weight of the polymer is about 500 kD for PDL, 70-150 kD for DEAE.DEX, 750 kD for PEI, 4 kD-6 kD for polybrene, 5.1 kD for protamine sulfate. The inventors believe that the lower the molecular weight of the cationic polymer, the more polymer is required in the complex in order to convert the negative charge of the phage such that it is positive at physiological pH.

Preferably, the cationic polymer comprises DEAE, more preferably DEAE.DEX. Preferably, the polymer comprises PDL. In some embodiments, the cationic polymer may comprise a combination of any of the polymers described herein, such as DEAE.DEX and PDL.

Preferably, the complex comprises a weight:weight ratio of about 50 ng-500 ng polymer:1 μg phage, more preferably about 100 ng-400 ng polymer:1 μg phage, and even more preferably about 130 ng-320 ng polymer:1 μg phage. In embodiments where the polymer is PDL, the complex preferably comprises a weight:weight ratio of about 50 ng-300 ng polymer:1 μg phage, more preferably about 100 ng-200 ng polymer:1 μg phage, and even more preferably about 120 ng-150 ng polymer:1 μg phage. In embodiments where the polymer is DEAE, the complex preferably comprises a weight:weight ratio of about 100 ng-500 ng polymer:1 μg phage, more preferably about 200 ng-400 ng polymer:1 μg phage, and even more preferably about 250 ng-350 ng polymer:1 μg phage.

In another embodiment, the bacteriophage-cationic polymer complex may comprise calcium phosphate. Advantageously, calcium phosphate increases cellular uptake of the bacteriophage-cationic polymer complex according to the invention (as shown in Example 7).

As explained in the Examples, the cationic polymer forms a complex with the bacteriophage, and preferably with the phage capsid protein. Preferably, the complex is created by electrostatic attraction between the polymer and proteins in the bacteriophage. Preferably, the polymer forms an outer coating on the bacteriophage, preferably on the capsid thereof.

Preferably, the ζ-potential of the bacteriophage-polymer complex is at least 5 mV, 10 mV or 15 mV at physiological pH. As shown in FIG. 4b, the presence of the polymer within the complex causes a marked increase in net charge of the resultant bacteriophage. The inventors hypothesise that this increase in ζ-potential can be attributed to surface adsorption of the polymer on the bacteriophage counteracting the inherent negative charge of the bacteriophage particles at physiological pH.

The inventors have developed a novel method for preparing the complex of the first aspect.

Hence, in a second aspect of the invention, there is provided a method of producing a targeted bacteriophage-polymer complex, the method comprising contacting a recombinant targeted-bacteriophage with a cationic polymer to form a stable complex, which has a net positive charge.

The bacteriophage and cationic polymer used in the method of the second aspect can be any of those chosen to form the recombinant bacteriophage-polymer complex of the first aspect. As discussed in the Examples, the inventors observed that the recombinant bacteriophage preferentially forms a stable and active bacteriophage-polymer complex, which enhances the transduction efficiency of a bacteriophage, if it is pre-incubated with the cationic polymer prior to use. The bacteriophage can be incubated with the cationic polymer at a temperature of about 15-30° C., or about 18-25° C., or preferably about 20-23° C. Preferably, the bacteriophage is incubated with the cationic polymer at about room temperature. Preferably, the bacteriophage is incubated with the cationic polymer for at least 5 mins, 10 mins or 15 mins. Preferably, the bacteriophage is incubated with the cationic polymer for less than 3 hours, 2 hours or 1 hour. This pre-incubation step of the phage and polymer is believed to be important for the production of an active bacteriophage-polymer complex.

The skilled person would appreciate that the length of time that the bacteriophage is incubated with the polymer depends upon the temperature at which the incubation occurs, the type of polymer and the type of bacteriophage. Hence, any of the temperatures described herein may be combined with any of the incubation times described herein. For instance, at higher temperatures, such as 25-30° C., the incubation step can be at least 10 minutes, while at lower temperatures, such as 20-25° C., the incubation step can be at least 15 minutes.

The inventors have observed that the complex of the first aspect can aggregate together to form larger, stable particles or "aggregates", which comprise a plurality of the bacteriophage-polymer complexes, and that these aggregates as a whole display an overall net positive charge at physiological pH.

Therefore, in a third aspect, there is provided an aggregate comprising a plurality of targeted bacteriophage-polymer complexes according to the first aspect.

As shown in the Examples, the aggregates of the invention are much larger (at least 6-7 times larger) than the phage on its own. For example, the mean particle size of the aggregate can be between about 600 nm and 2500 nm. Preferably, the mean particle size of the aggregate is between about 600 nm and 1500 nm, or preferably between about 700 nm and 1200 nm. The aggregate can comprise at least 5, 10, 50 or 100 bacteriophage-polymer complexes.

The inventors have demonstrated that the bacteriophage-polymer complexes of the invention can be efficiently targeted to, and transduce tumor cells, which are subsequently killed. However, it will be appreciated that the type of cell, which is targeted by the complex depends on the type of cell-targeting ligand expressed on the surface of the bacteriophage. In the Examples, tumor cells are used illustratively to show that the complex of the invention exhibit a significantly improved transduction.

Thus, in a fourth aspect, there is provided the targeted bacteriophage-polymer complex according to the first aspect or the aggregate according to the third aspect, for use in therapy or diagnosis.

The invention may be used for the treatment of a wide variety of diseases due to the target-specific nature and the improved transduction efficiency of the recombinant bacteriophage-polymer complex of the invention. Consequently, the therapeutic opportunities of recombinant bacteriophages used in gene therapy may be significantly increased by the invention due to (i) minimisation of any side-effects, which may occur due to off-target effects of the recombinant bacteriophage, and (ii) significantly improved target-specific cellular transduction. The invention may be used prophylactically to prevent disease, or after the development of a disease, to ameliorate/treat it.

Hence, in a fifth aspect, there is provided the targeted bacteriophage-polymer complex according to the first aspect or the aggregate according to the third aspect, for use in a gene therapy technique.

In a sixth aspect, there is provided a method of treating, preventing or ameliorating a disease in a subject using a gene therapy technique, the method comprising administering, to a subject in need of such treatment, a therapeutically effective amount of the targeted bacteriophage-polymer complex according to the first aspect or the aggregate according to the third aspect.

It will be appreciated that the invention may also be used to create a variety of different bacteriophage-polymer complex vectors that can be used for the treatment and/or diagnosis of a variety of diseases depending on the nature of the recombinant bacteriophage and the cationic polymer used. For example, in an embodiment where the bacteriophage comprises a tumor-targeting ligand and/or which comprises a transgene expressing an anti-tumor protein (e.g. the HSVtk gene), then it may be used to treat cancer. Hence, the target cell in the gene therapy technique is preferably eukaryotic, and preferably mammalian.

The inventors have clearly demonstrated that the multifunctional bacteriophage of the invention exhibits elevated transgene expression in a transduced target cell. Hence, they believe that the phage will have a significant commercial value in the delivery of vaccines.

Thus, in a seventh aspect, there is provided a vaccine comprising the bacteriophage according to the first aspect, or the aggregate according to the third aspect.

In an eighth aspect, there is provided use of the bacteriophage according to the first aspect, or the aggregate according to the third aspect, for vaccine delivery.

The vaccine is preferably a DNA vaccine. The vaccine preferably comprises a suitable adjuvant. In an embodiment, the bacteriophage vector may be used to carry a transgene or DNA cassette encoding an antigen to stimulate the body's immune system. The phage may also be used to directly display and express the antigen of interest, thus providing a unique platform for the simultaneous delivery, by a single phage particle, of numerous antigens as vaccine DNA vaccines or proteins readily expressed on the phage surface.

The inventors believe that the bacteriophage-polymer complex or aggregate of the invention can also be used in a variety of different genetic-molecular imaging techniques, such as positron emission tomography (PET) or SPECT imaging.

Hence, in a ninth aspect there is provided use of the bacteriophage-polymer complex according to the first aspect, or the aggregate according to the third aspect, in a genetic-molecular imaging technique.

The transgene may encode HSVtk and/or the sodium/iodide symporter (NIS), and the complex or aggregate is preferably used in combination with a radiolabelled substrate. For example, the human sodium/iodide symporter (NIS) imaging gene is preferably used in combination with $I^{124}$ for clinically applicable positron emission tomography (PET) imaging or $I^{125}/^{99m}Tc$-pertechnetate for clinically applicable SPECT imaging.

Alternatively, the HSVtk gene is preferably used in combination with radiolabeled nucleoside analogues such as the 20-[18F]-fluoro-20-deoxy-1-b-D-arabino-furanosyl-5-ethyluracil ([18F]FEAU).

It will be appreciated that the recombinant bacteriophage-polymer complex according to the first aspect or the aggregate according to the third aspect (i.e. both of which are referred to hereinafter as "agents") may be used in a medicament which may be used in a monotherapy, or as an adjunct to, or in combination with, known therapies for treating, ameliorating, or preventing disease, such as cancer. The agents according to the invention may be combined in compositions having a number of different forms depending, in particular, on the manner in which the composition is to be used. Thus, for example, the composition may be in the form of a powder, tablet, capsule, liquid etc. or any other suitable form that may be administered to a person or animal in need of treatment. It will be appreciated that the vehicle of medicaments according to the invention should be one which is well-tolerated by the subject to whom it is given.

Medicaments comprising the agents according to the invention (i.e. the complex or aggregate) may be used in a number of ways. For instance, oral administration may be required, in which case the agents may be contained within a composition that may, for example, be ingested orally in the form of a tablet, capsule or liquid. Compositions comprising agents of the invention may be administered by inhalation (e.g. intranasally). Compositions may also be formulated for topical use. For instance, creams or ointments may be applied to the skin.

Agents according to the invention may also be incorporated within a slow- or delayed-release device. Such devices may, for example, be inserted on or under the skin, and the medicament may be released over weeks or even months. The device may be located at least adjacent the treatment site. Such devices may be particularly advantageous when long-term treatment with agents used according to the invention is required and which would normally require frequent administration (e.g. at least daily injection).

In a preferred embodiment, agents and compositions according to the invention may be administered to a subject by injection into the blood stream or directly into a site requiring treatment. Injections may be intravenous (bolus or infusion) or subcutaneous (bolus or infusion), or intradermal (bolus or infusion).

It will be appreciated that the amount of the agent that is required is determined by its biological activity and bio-availability, which in turn depends on the mode of administration, the physiochemical properties of the agent, and whether it is being used as a monotherapy, or in a combined therapy. The frequency of administration will also be influenced by the half-life of the agent within the subject being treated. Optimal dosages to be administered may be determined by those skilled in the art, and will vary with the particular agent in use, the strength of the pharmaceutical composition, the mode of administration, and the advancement of the disease. Additional factors depending on the particular subject being treated will result in a need to adjust dosages, including subject age, weight, gender, diet, and time of administration.

Generally, a daily dose of between 0.01 μg/kg of body weight and 500 mg/kg of body weight of the agent according to the invention may be used. More preferably, the daily dose is between 0.01 mg/kg of body weight and 400 mg/kg of body weight, and more preferably between 0.1 mg/kg and 200 mg/kg body weight.

As discussed in the Examples, the recombinant bacteriophage-polymer complex or aggregate may be administered before, during the or after the onset of disease. For example, the recombinant bacteriophage-polymer complex or aggregate may be administered immediately after a subject has developed a disease. Daily doses may be given systemically as a single administration (e.g. a single daily injection). Alternatively, the recombinant bacteriophage-polymer complex or aggregate may require administration twice or more times during a day. As an example, recombinant bacteriophage-polymer complex or aggregate may be administered as two (or more depending upon the severity of the disease being treated) daily doses of between 25 mg and 7000 mg (i.e. assuming a body weight of 70 kg). A patient receiving treatment may take a first dose upon waking and then a second dose in the evening (if on a two dose regime) or at 3- or 4-hourly intervals thereafter. Alternatively, a slow release device may be used to provide optimal doses of recombinant bacteriophage-polymer complex or aggregate according to the invention to a patient without the need to administer repeated doses.

Known procedures, such as those conventionally employed by the pharmaceutical industry (e.g. in vivo experimentation, clinical trials, etc.), may be used to form specific formulations comprising the complex or aggregate according to the invention and precise therapeutic regimes (such as daily doses of the complex or aggregate and the frequency of administration).

Hence, in a tenth aspect of the invention, there is provided a pharmaceutical composition, comprising the targeted bacteriophage-polymer complex of the first aspect or the aggregate of the third aspect, and a pharmaceutically acceptable vehicle.

The composition can be used in the therapeutic amelioration, prevention or treatment of any disease in a subject that is treatable with gene therapy, such as cancer.

The invention also provides, in an eleventh aspect, a process for making the pharmaceutical composition according to the tenth aspect, the process comprising contacting a therapeutically effective amount of the targeted bacteriophage-polymer complex of the first aspect or the aggregate of the third aspect, and a pharmaceutically acceptable vehicle.

A "subject" may be a vertebrate, mammal, or domestic animal. Hence, agents, compositions and medicaments according to the invention may be used to treat any mammal, for example livestock (e.g. a horse), pets, or may be used in other veterinary applications. Most preferably, however, the subject is a human being.

A "therapeutically effective amount" of agent is any amount which, when administered to a subject, is the amount of drug that is needed to treat the target disease, or produce the desired effect, e.g. result in tumor killing.

For example, the therapeutically effective amount of agent used may be from about 0.01 mg to about 800 mg, and preferably from about 0.01 mg to about 500 mg.

A "pharmaceutically acceptable vehicle" as referred to herein, is any known compound or combination of known compounds that are known to those skilled in the art to be useful in formulating pharmaceutical compositions.

In one embodiment, the pharmaceutically acceptable vehicle may be a solid, and the composition may be in the form of a powder or tablet. A solid pharmaceutically acceptable vehicle may include one or more substances which may also act as flavouring agents, lubricants, solubilisers, suspending agents, dyes, fillers, glidants, compression aids, inert binders, sweeteners, preservatives, dyes, coatings, or tablet-disintegrating agents. The vehicle may also be an encapsulating material. In powders, the vehicle is a finely divided solid that is in admixture with the finely divided active agents according to the invention. In tablets, the active agent (e.g. the recombinant bacteriophage-polymer hybrid vector or the aggregate of the invention) may be mixed with a vehicle having the necessary compression properties in suitable proportions and compacted in the shape and size desired. The powders and tablets preferably contain up to 99% of the active agents. Suitable solid vehicles include, for example calcium phosphate, magnesium stearate, talc, sugars, lactose, dextrin, starch, gelatin, cellulose, polyvinylpyrrolidine, low melting waxes and ion exchange resins. In another embodiment, the pharmaceutical vehicle may be a gel and the composition may be in the form of a cream or the like.

However, the pharmaceutical vehicle may be a liquid, and the pharmaceutical composition is in the form of a solution. Liquid vehicles are used in preparing solutions, suspensions, emulsions, syrups, elixirs and pressurized compositions. The recombinant bacteriophage-polymer vector according to the invention may be dissolved or suspended in a pharmaceutically acceptable liquid vehicle such as water, an organic solvent, a mixture of both or pharmaceutically acceptable oils or fats. The liquid vehicle can contain other suitable pharmaceutical additives such as solubilisers, emulsifiers, buffers, preservatives, sweeteners, flavouring agents, suspending agents, thickening agents, colours, viscosity regulators, stabilizers or osmo-regulators. Suitable examples of liquid vehicles for oral and parenteral administration include water (partially containing additives as above, e.g. cellulose derivatives, preferably sodium carboxymethyl cellulose solution), alcohols (including monohydric alcohols and polyhydric alcohols, e.g. glycols) and their derivatives, and oils (e.g. fractionated coconut oil and arachis oil). For parenteral administration, the vehicle can also be an oily ester such as ethyl oleate and isopropyl myristate. Sterile liquid vehicles are useful in sterile liquid form compositions for parenteral administration. The liquid vehicle for pressurized compositions can be a halogenated hydrocarbon or other pharmaceutically acceptable propellant.

Liquid pharmaceutical compositions, which are sterile solutions or suspensions, can be utilized by, for example, intramuscular, intrathecal, epidural, intraperitoneal, intravenous and particularly subcutaneous injection. The recombinant bacteriophage-polymer (hybrid) vector may be prepared as a sterile solid composition that may be dissolved or suspended at the time of administration using sterile water, saline, or other appropriate sterile injectable medium.

The recombinant bacteriophage-polymer complex or aggregate and pharmaceutical compositions of the invention may be administered orally in the form of a sterile solution or suspension containing other solutes or suspending agents (for example, enough saline or glucose to make the solution isotonic), bile salts, acacia, gelatin, sorbitan monoleate, polysorbate 80 (oleate esters of sorbitol and its anhydrides copolymerized with ethylene oxide) and the like. The recombinant bacteriophage-polymer (hybrid) vector according to the invention can also be administered orally either in liquid or solid composition form. Compositions suitable for oral administration include solid forms, such as pills, capsules, granules, tablets, and powders, and liquid forms, such as solutions, syrups, elixirs, and suspensions. Forms useful for parenteral administration include sterile solutions, emulsions, and suspensions.

All of the features described herein (including any accompanying claims, abstract and drawings), and/or all of the steps of any method or process so disclosed, may be combined with any of the above aspects in any combination, except combinations where at least some of such features and/or steps are mutually exclusive.

Figure 1B:
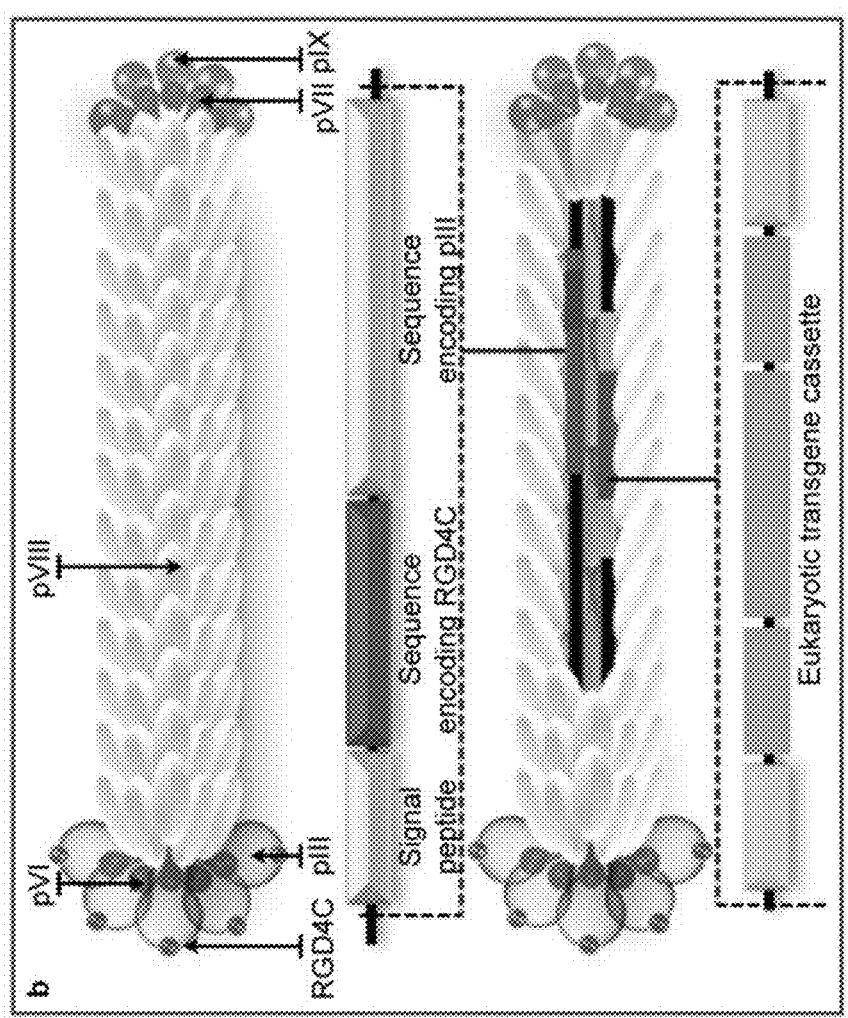
Figure 2A:
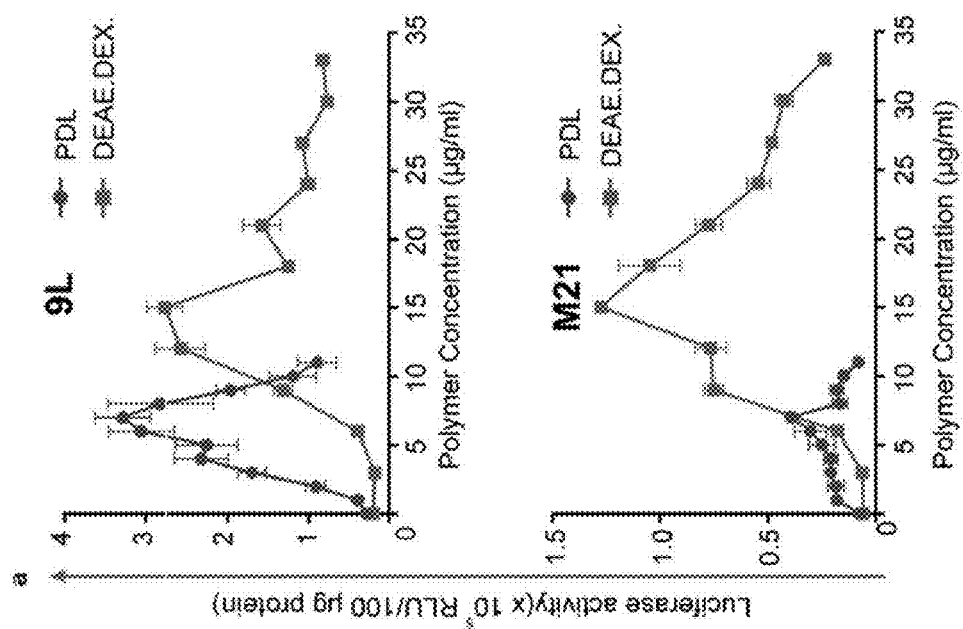
Figure 2B:
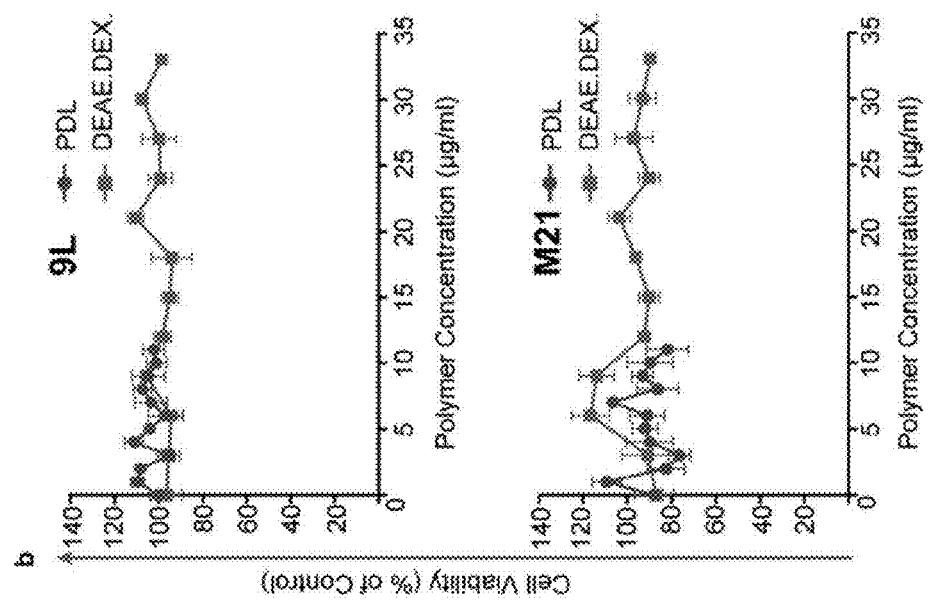
Figure 3A:
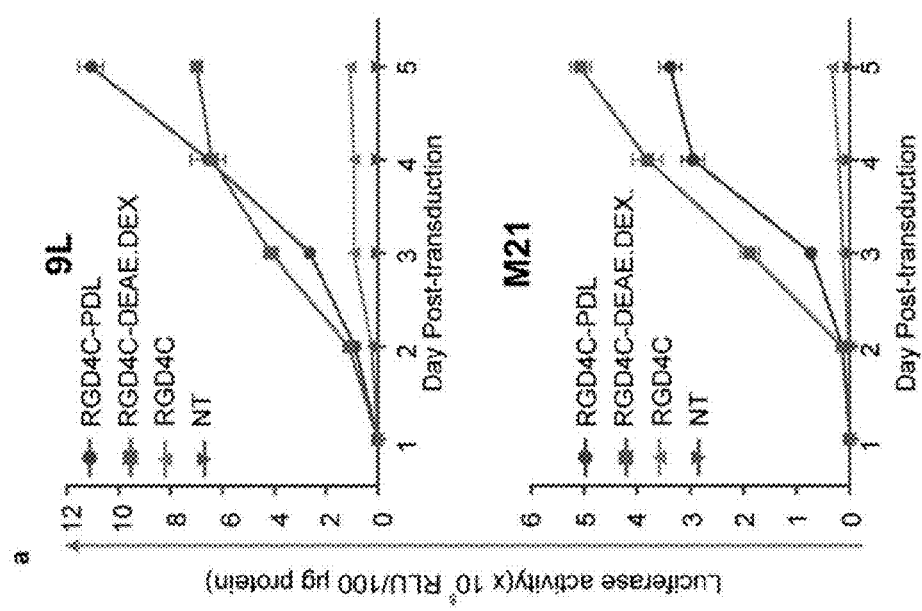
Figure 3B:
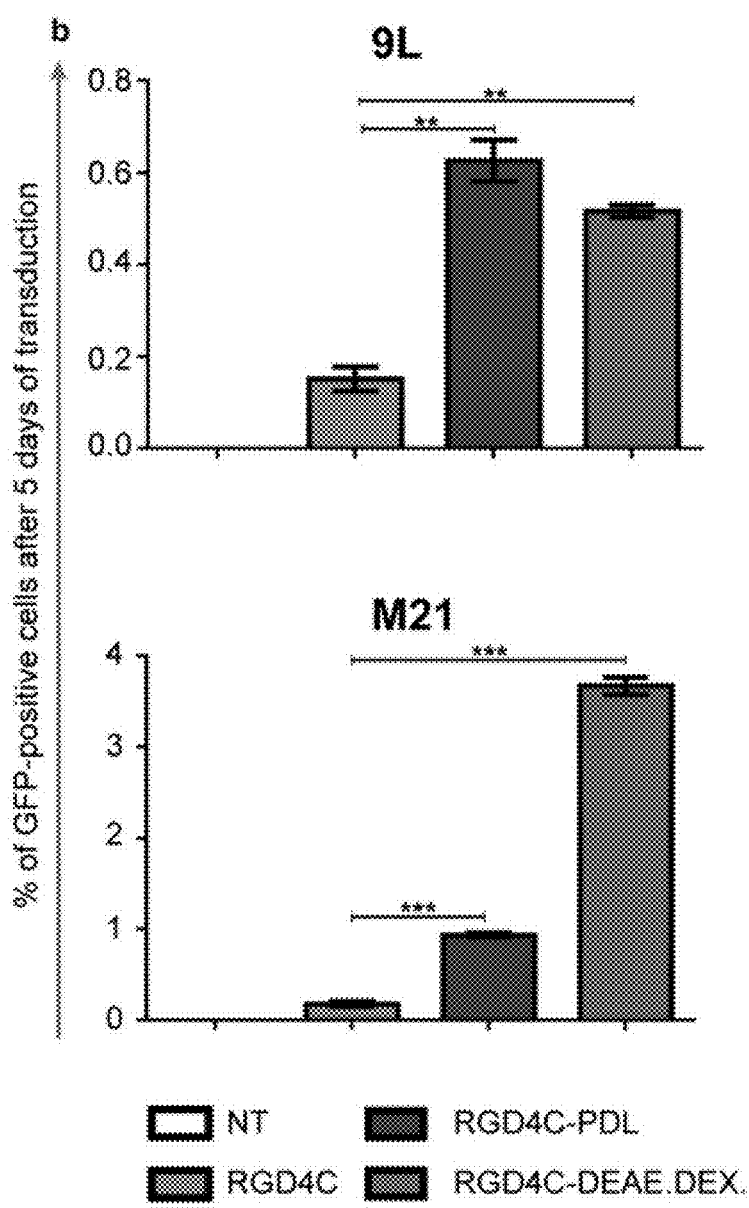
Figure 3C:
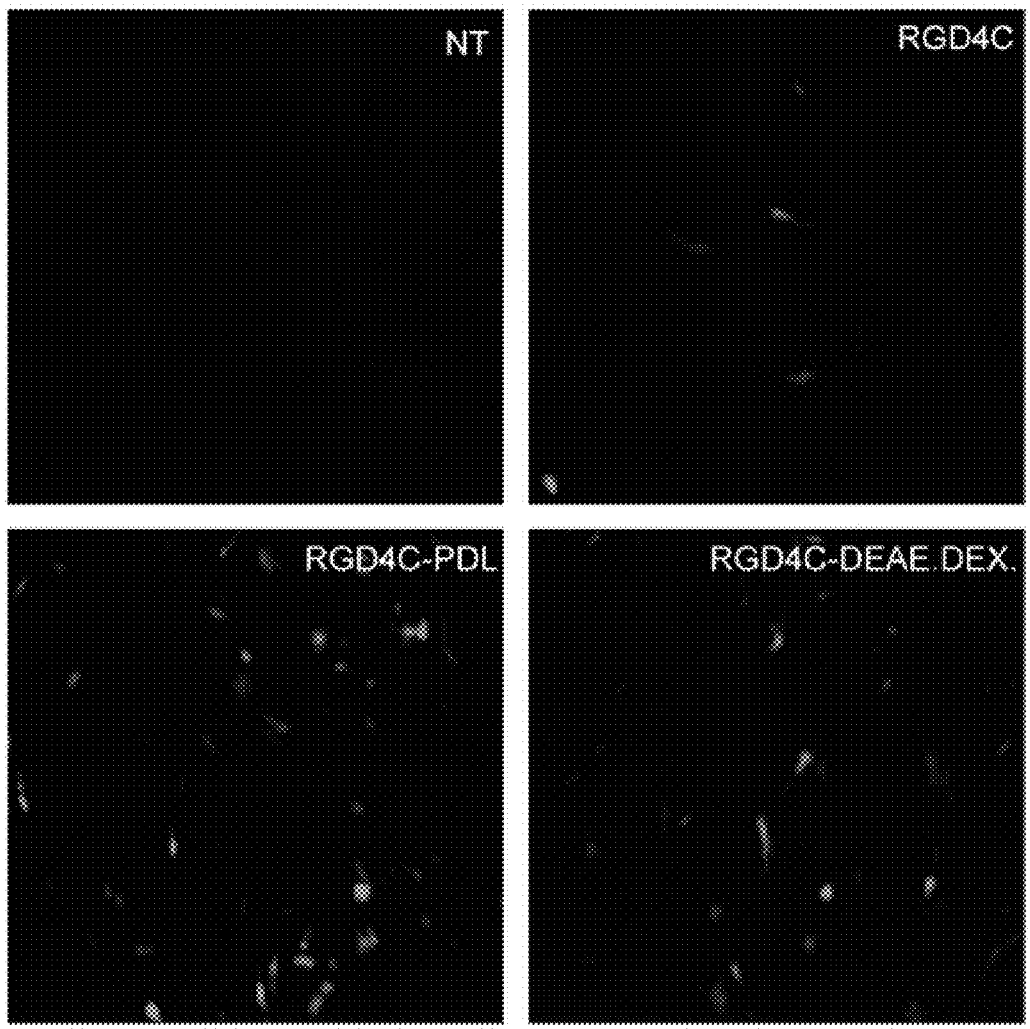
Figure 4A:
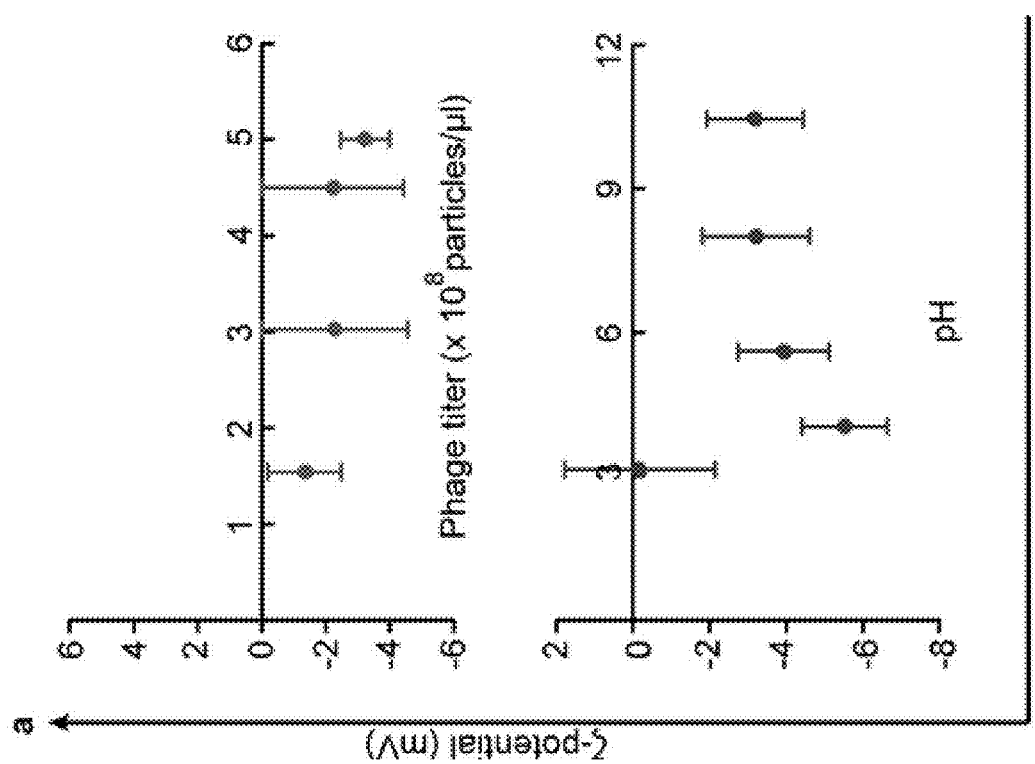
Figure 4B:
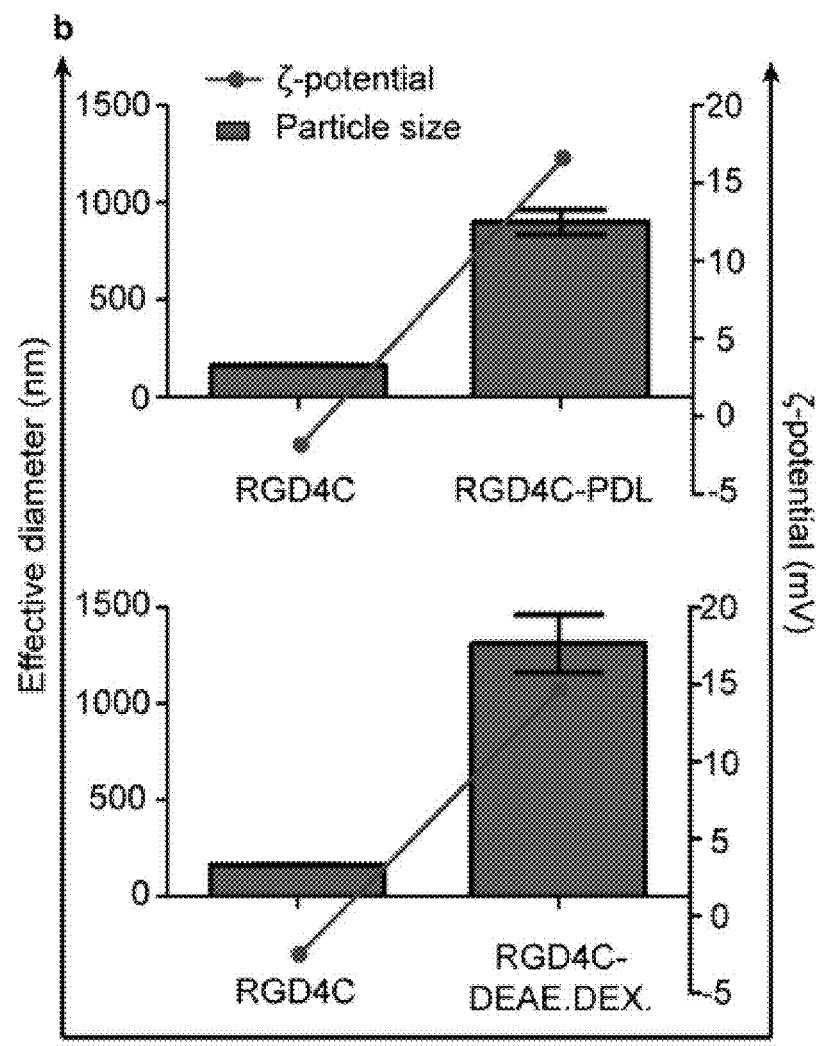
Figure 4C:
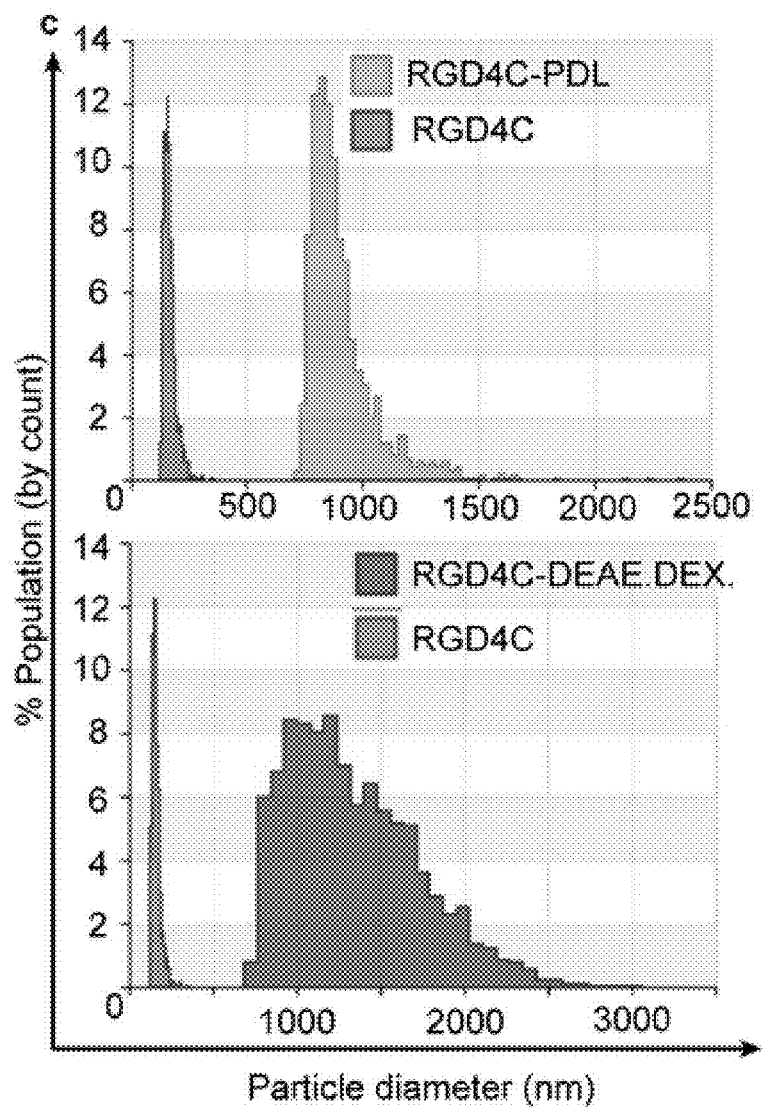
Figure 4D:
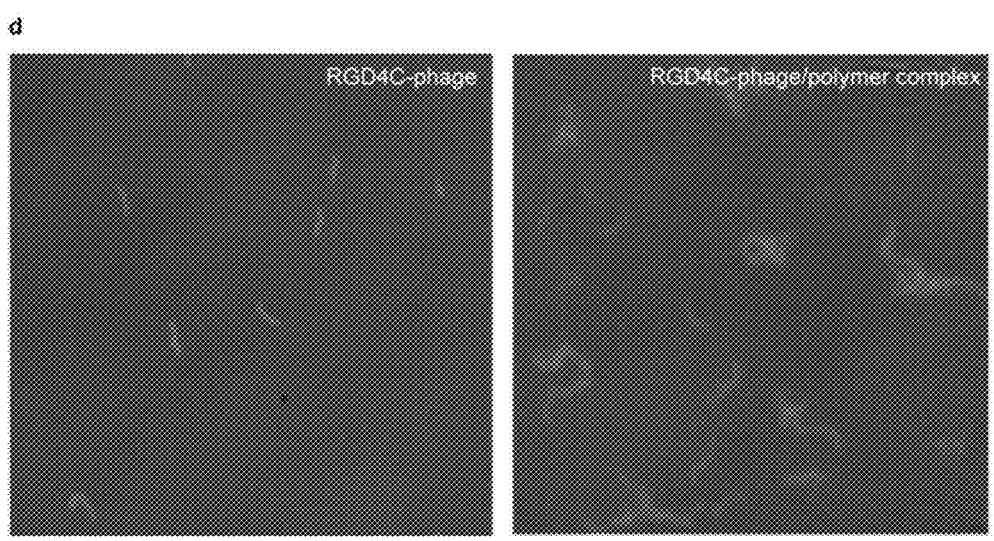
Figure 5A:
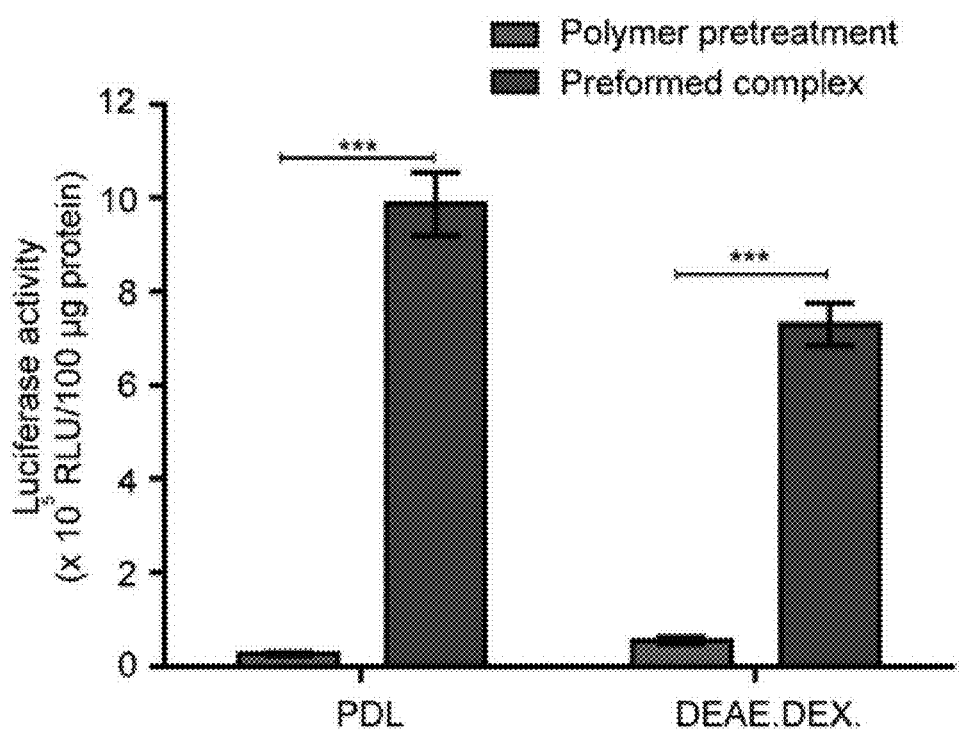
Figure 5B:
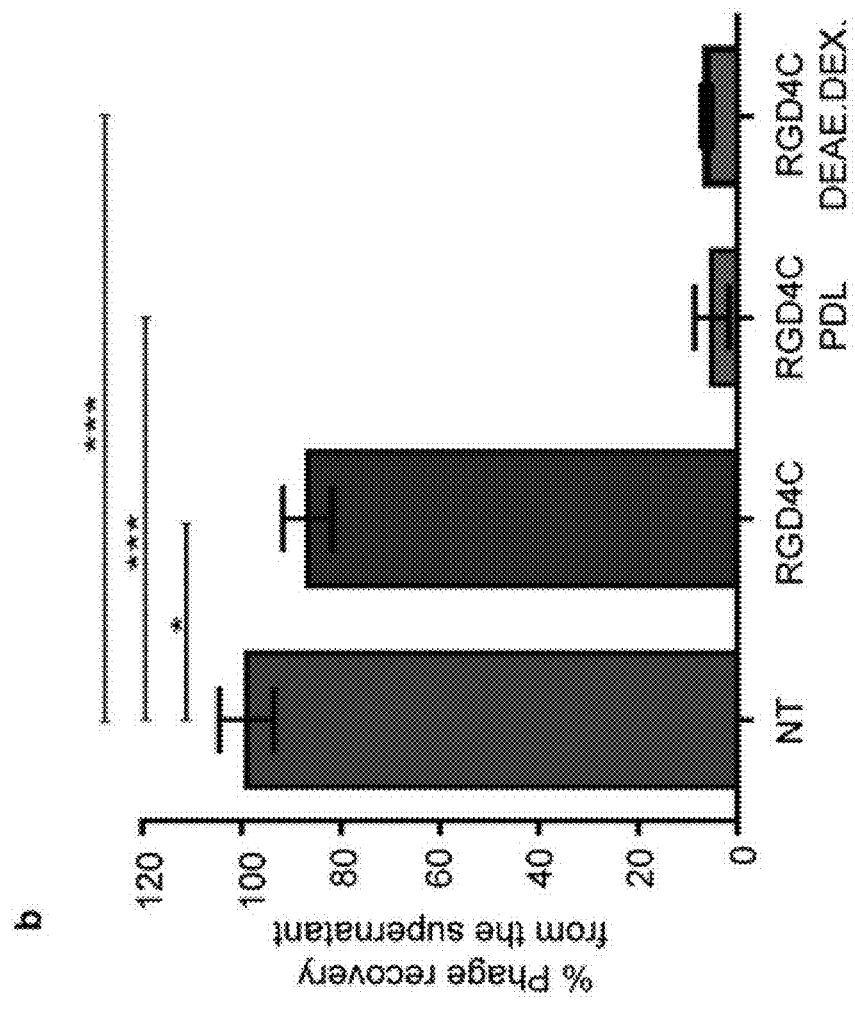
Figure 5C:
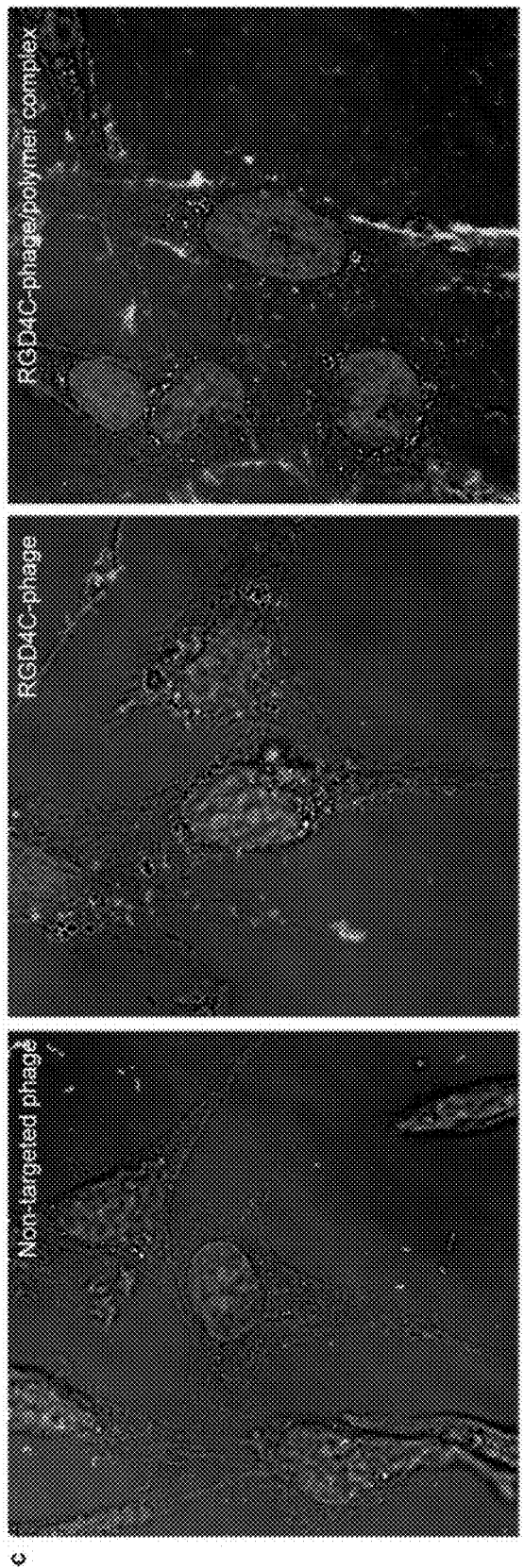
Figure 6A:
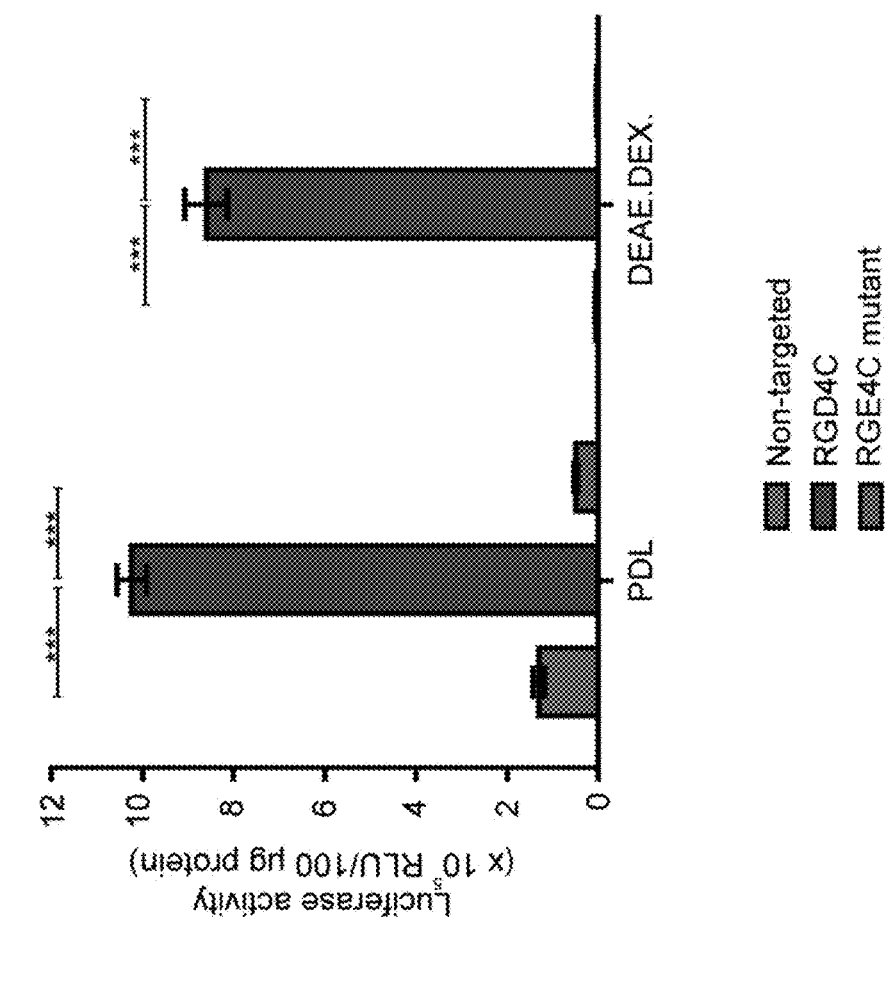
Figure 6B:
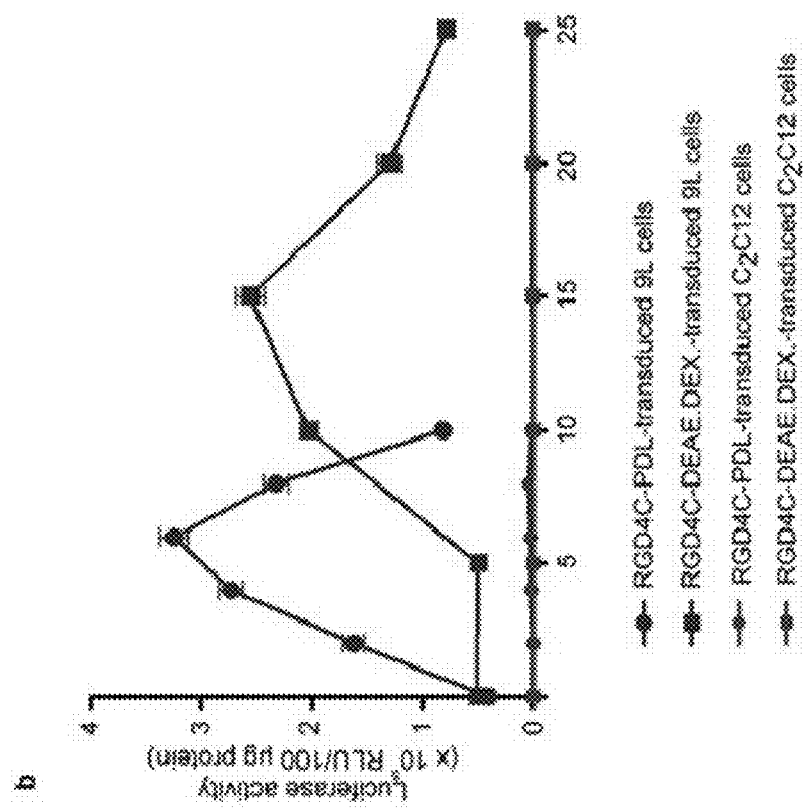
Figure 6C:
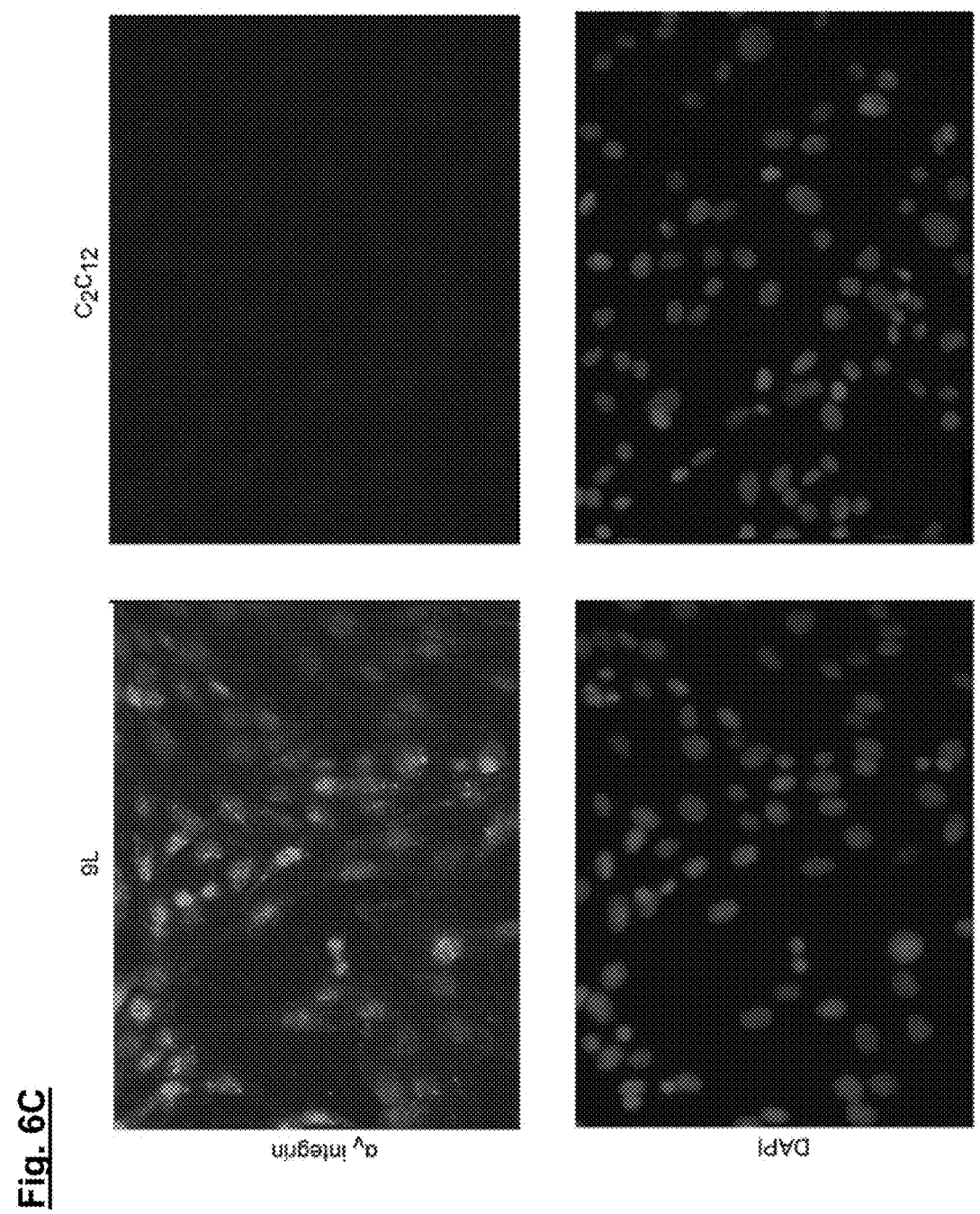
Figure 7A:
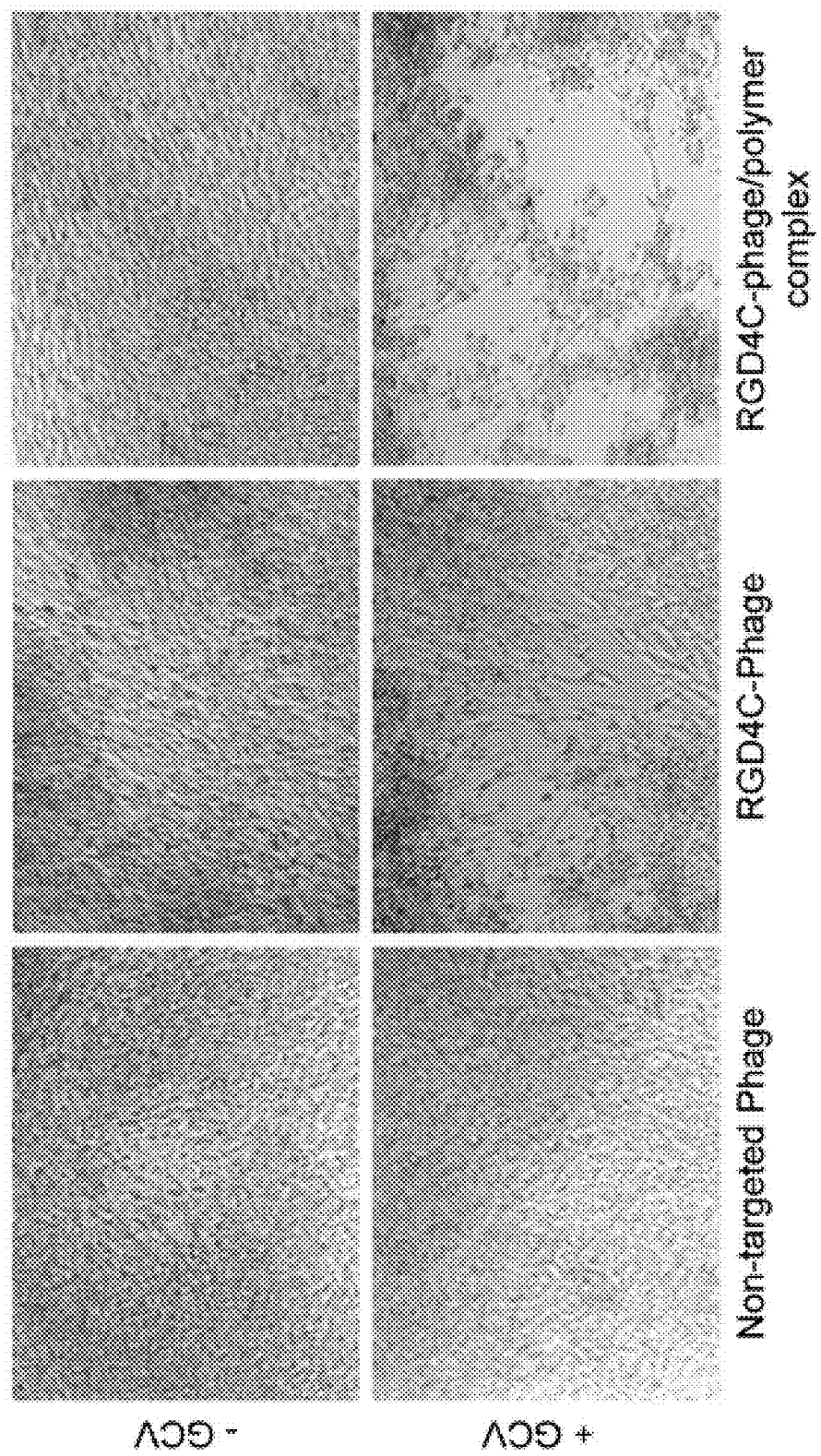
Figure 8:
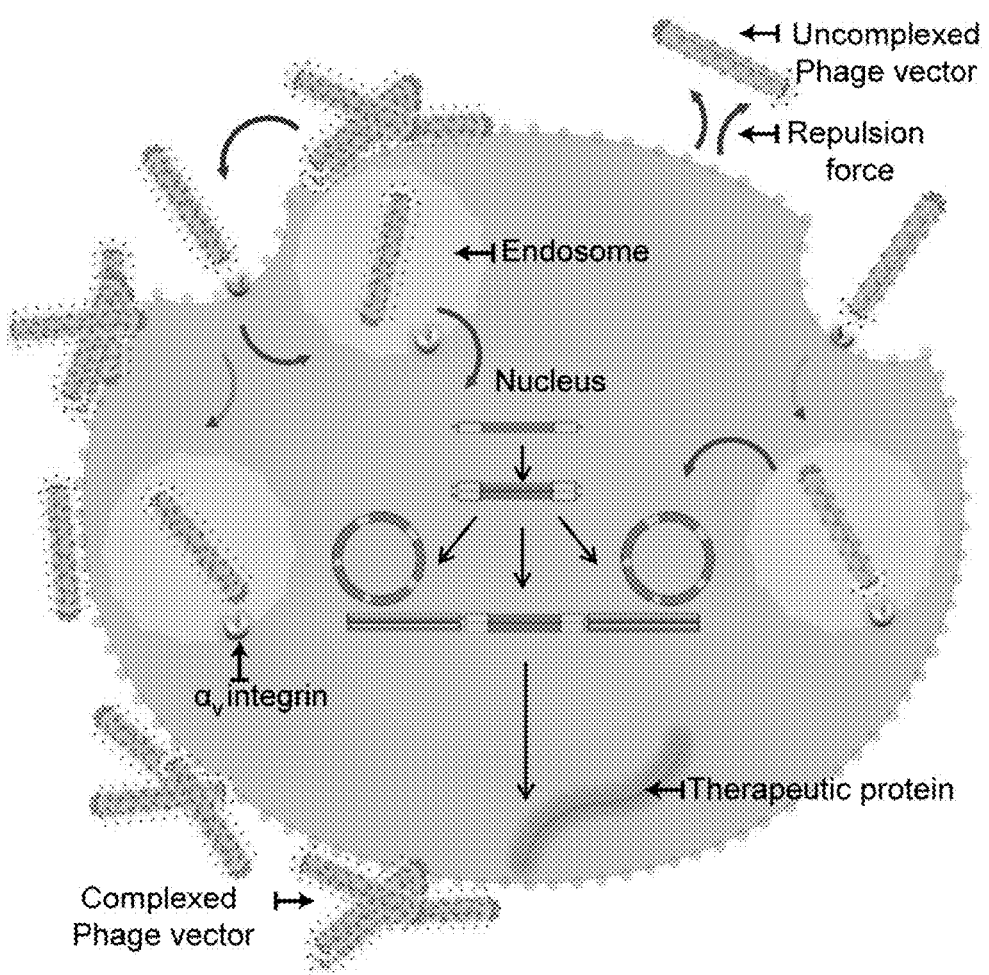
Figure 9:
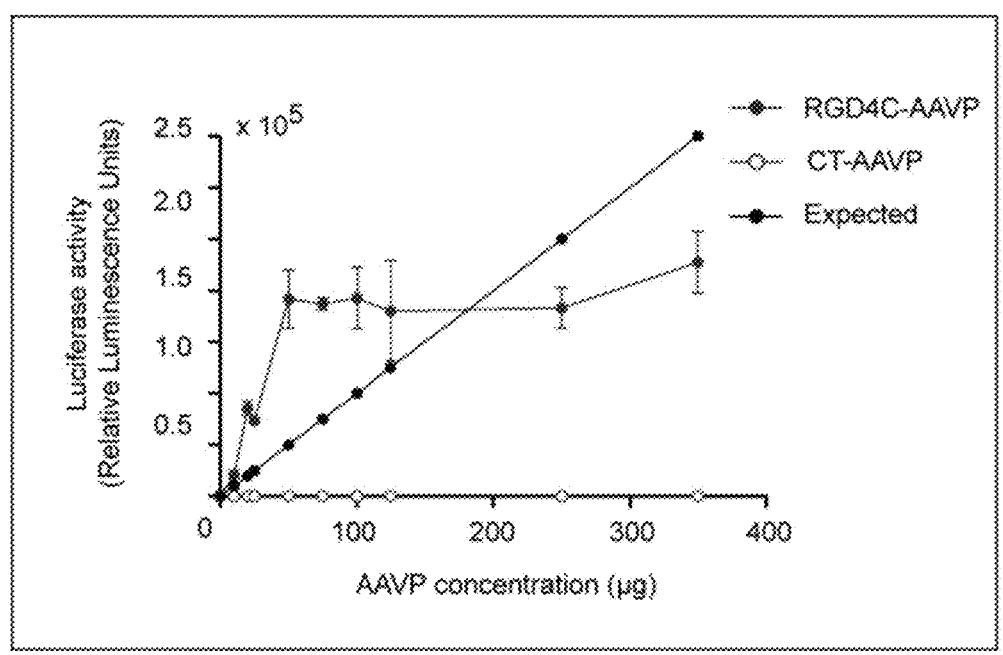
Figure 10A:
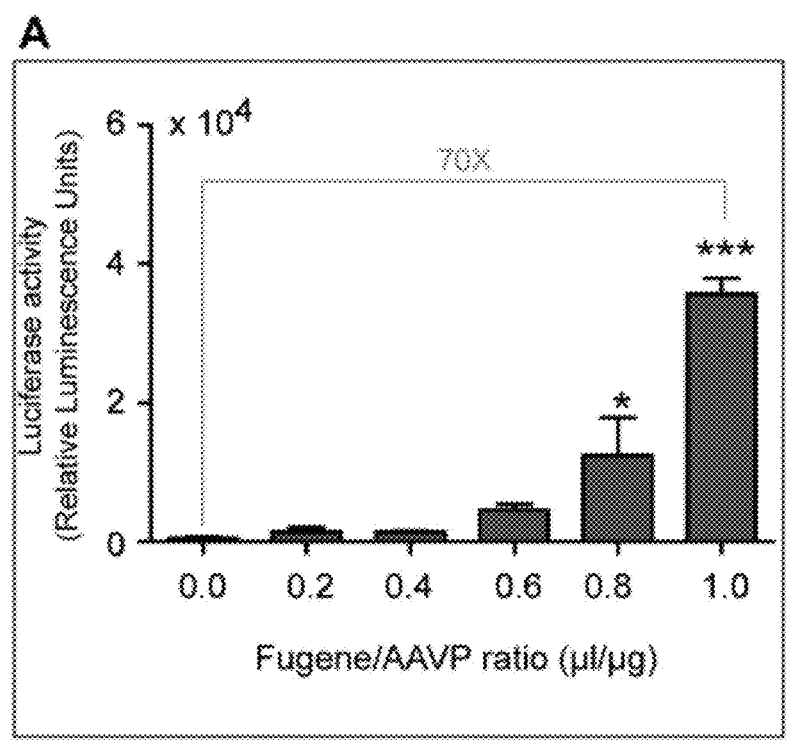
Figure 10B:
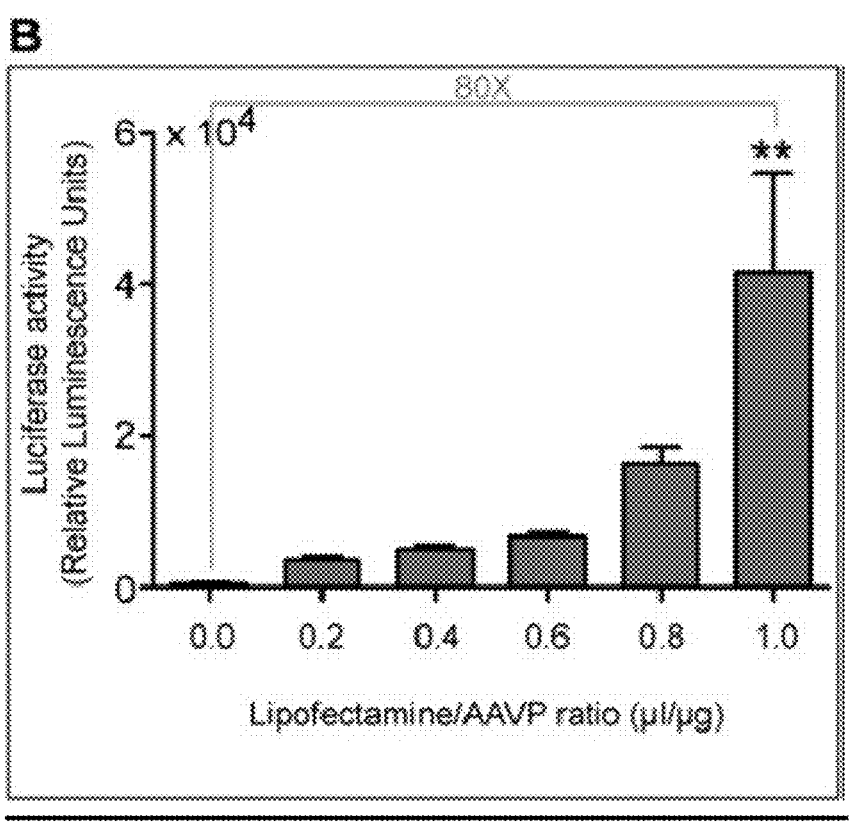
Figure 10C:
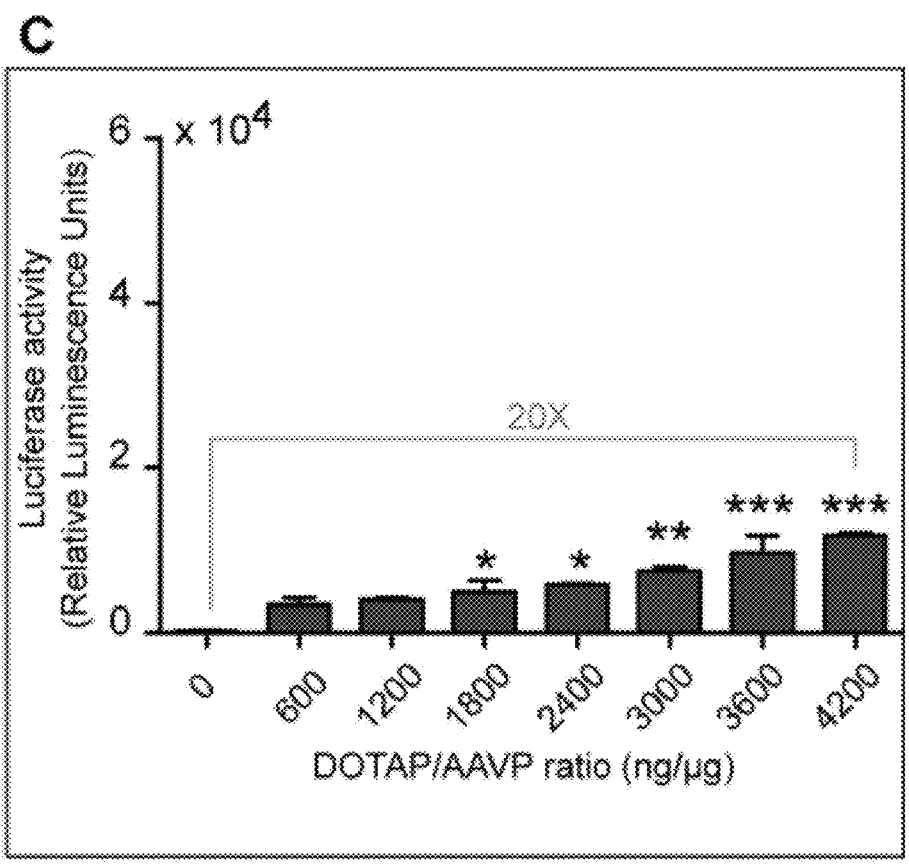
Figure 10D:
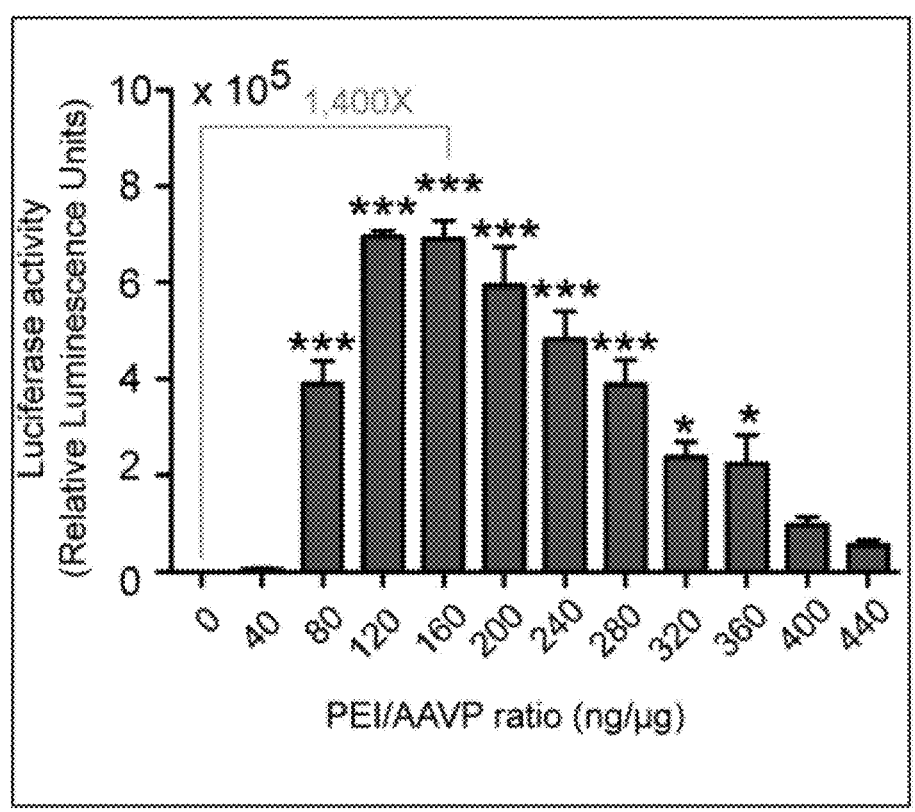
Figure 10E:
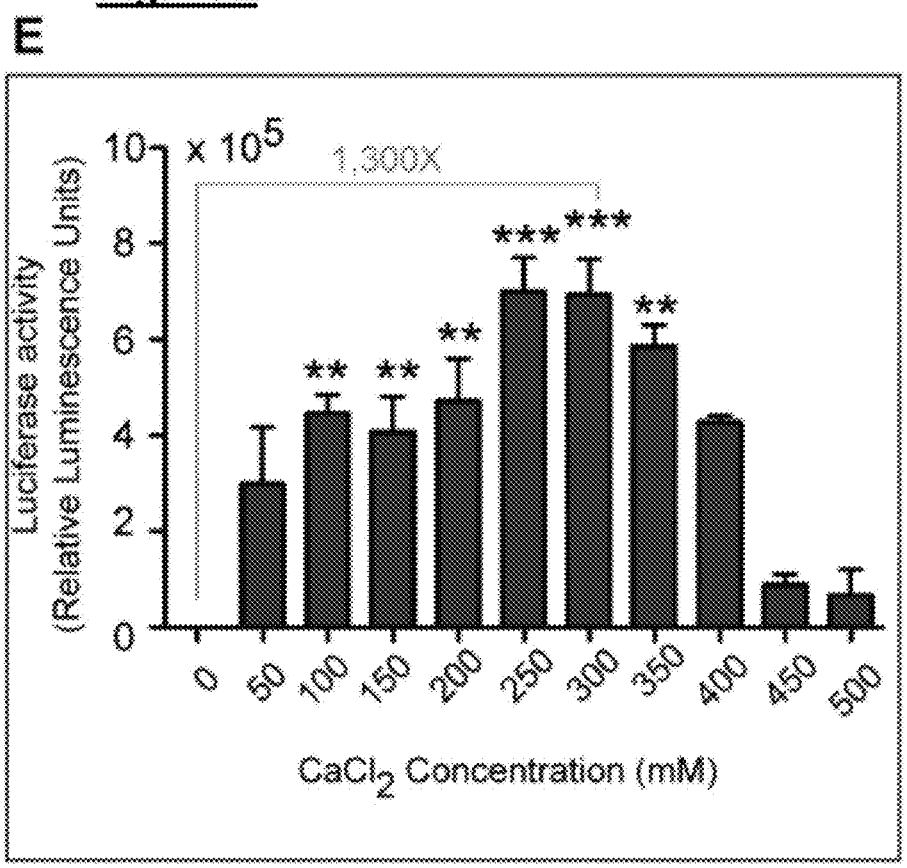
Figure 10F:
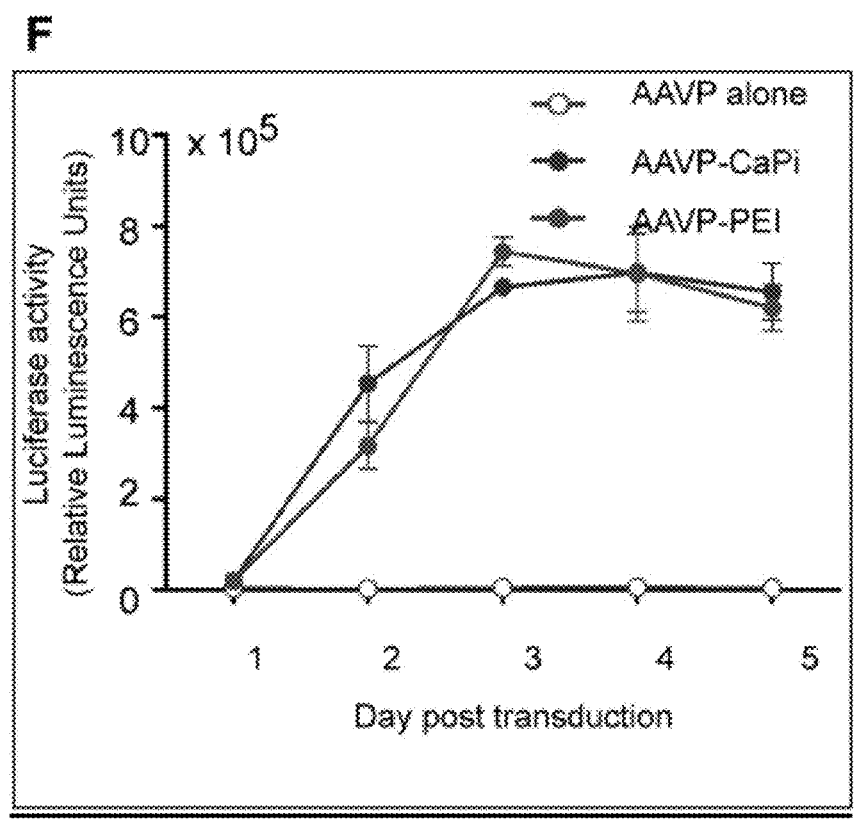
Figure 11:
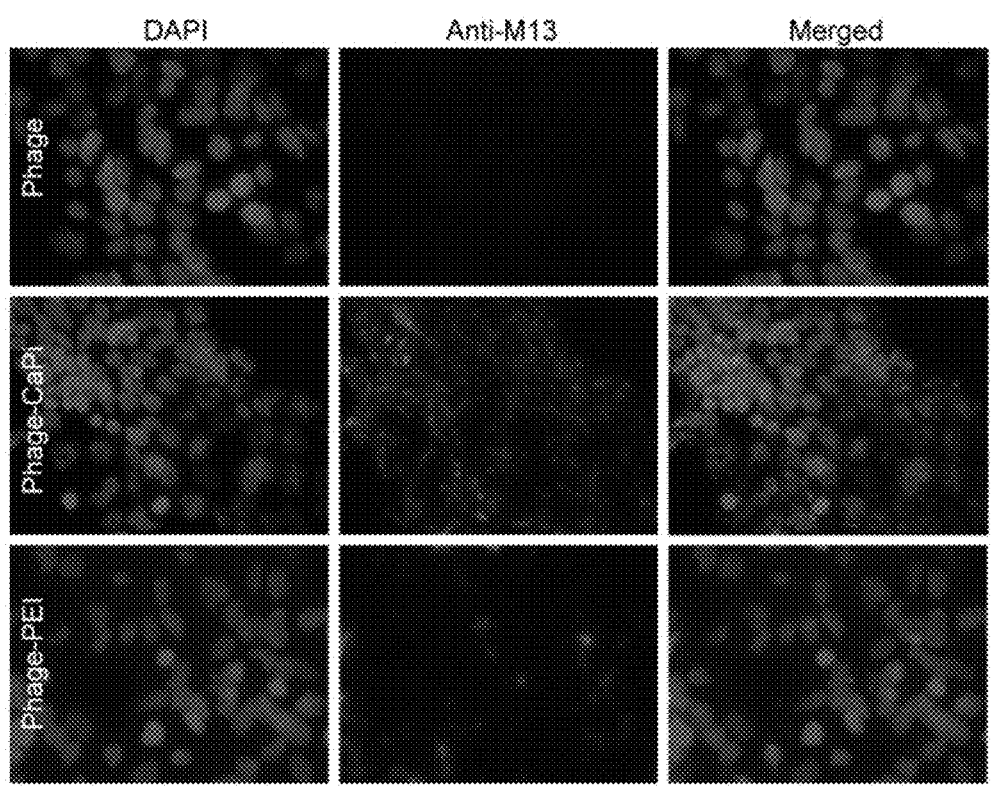
Figure 12A:
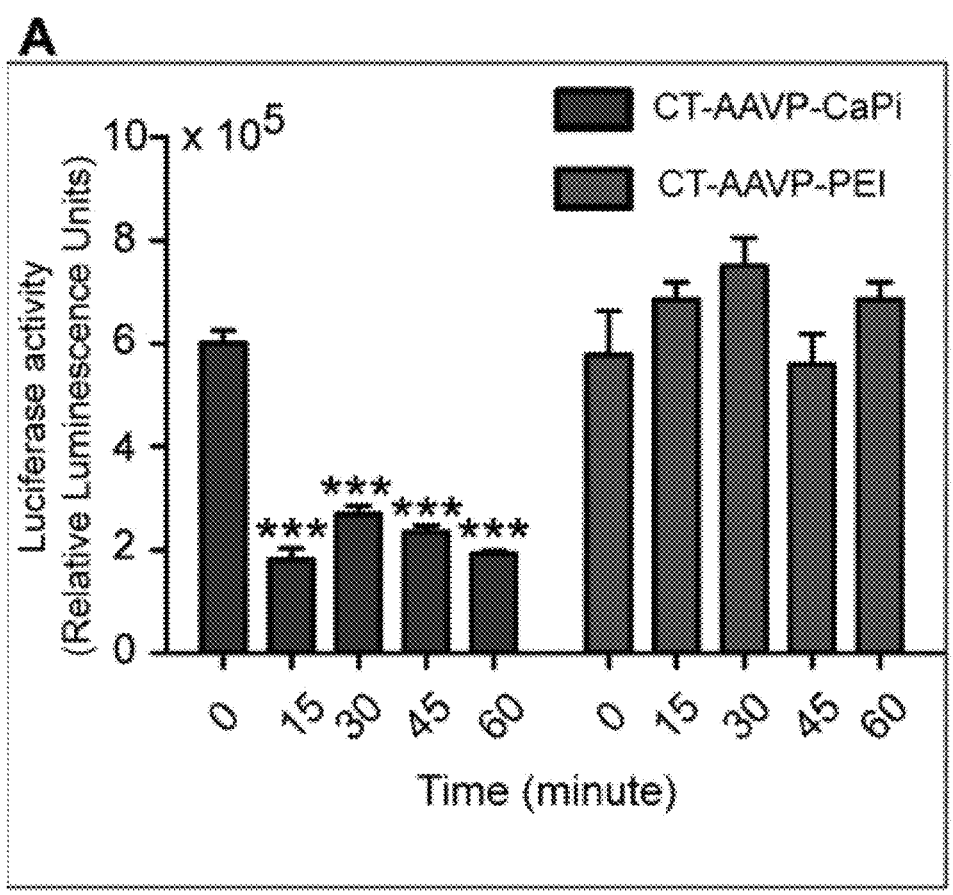
Figure 12B:
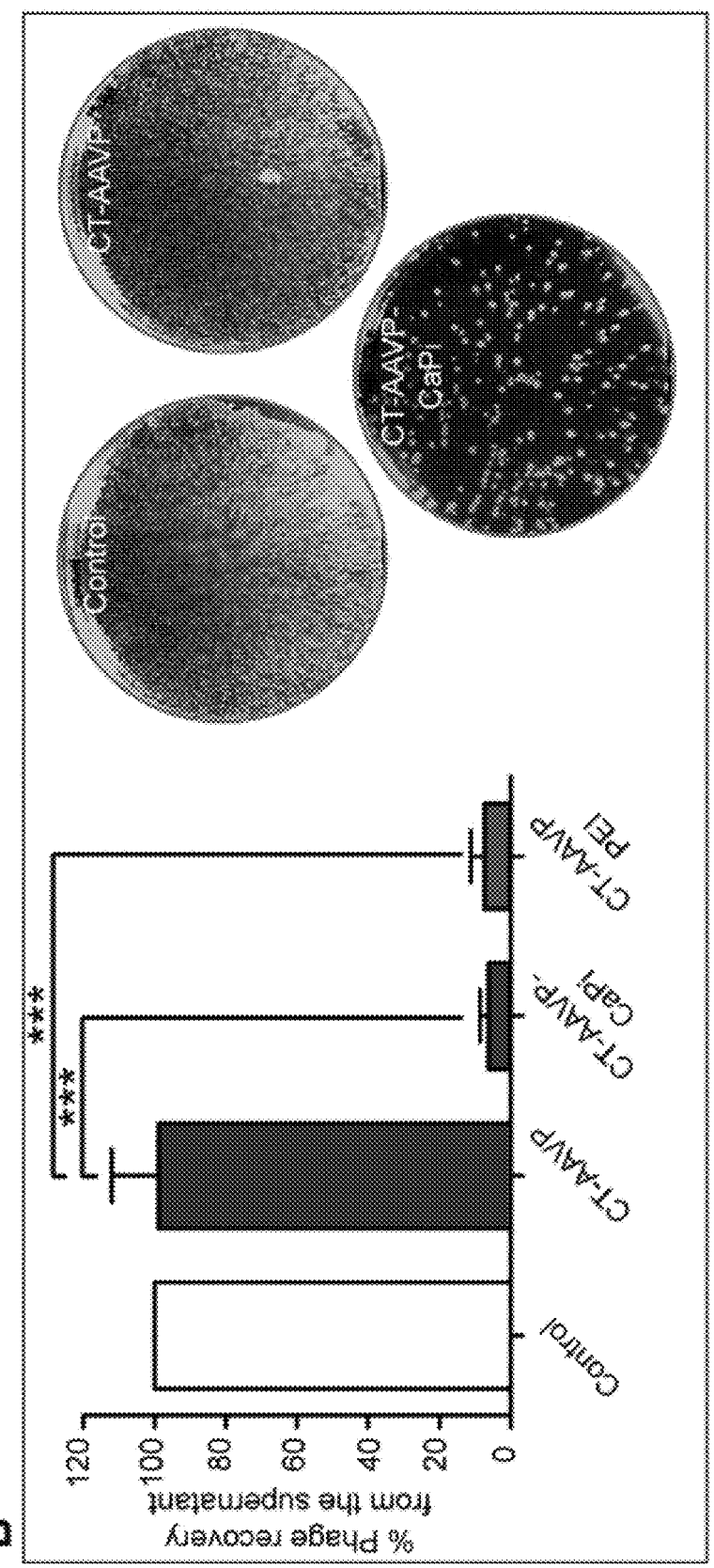
Figure 12C:
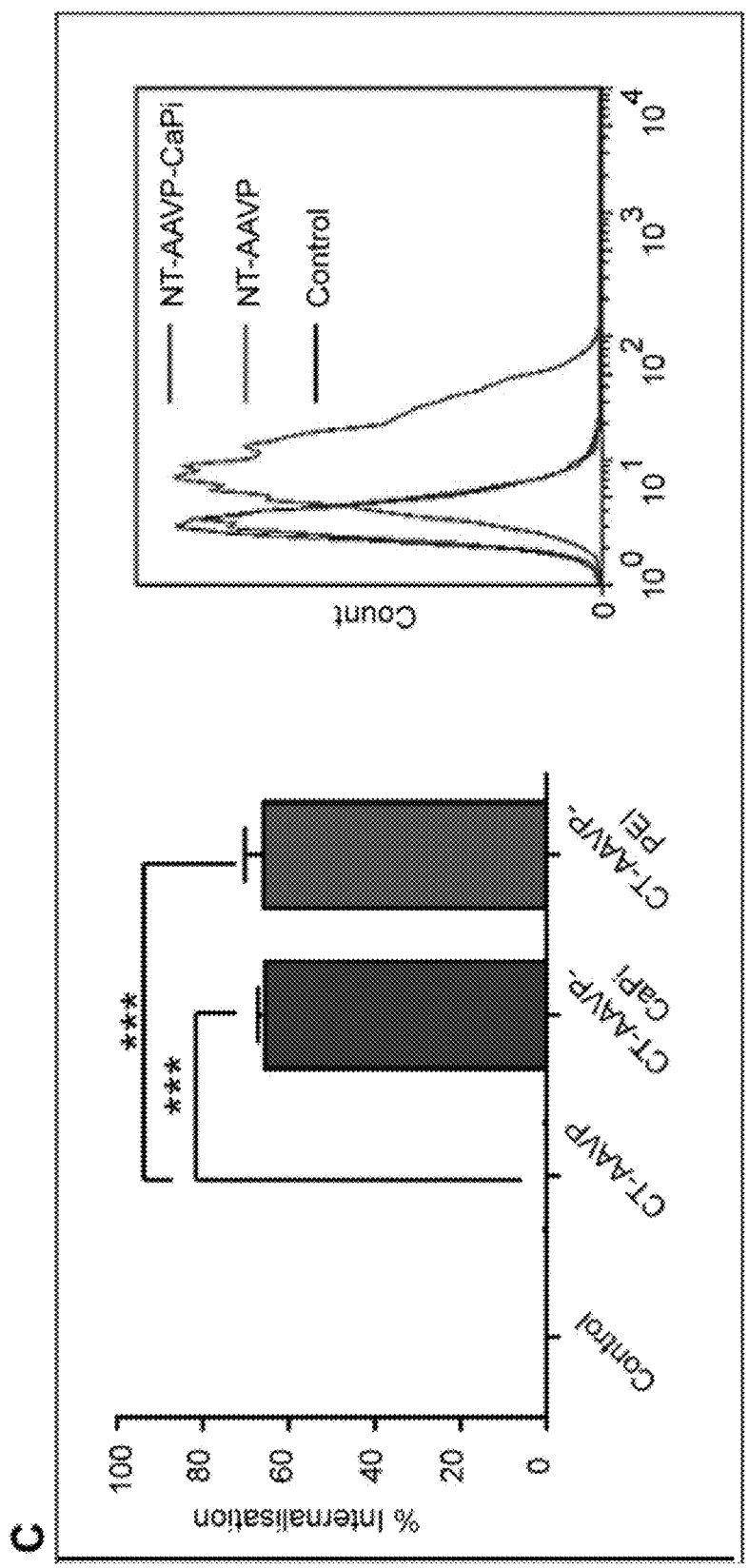
Figure 12D:
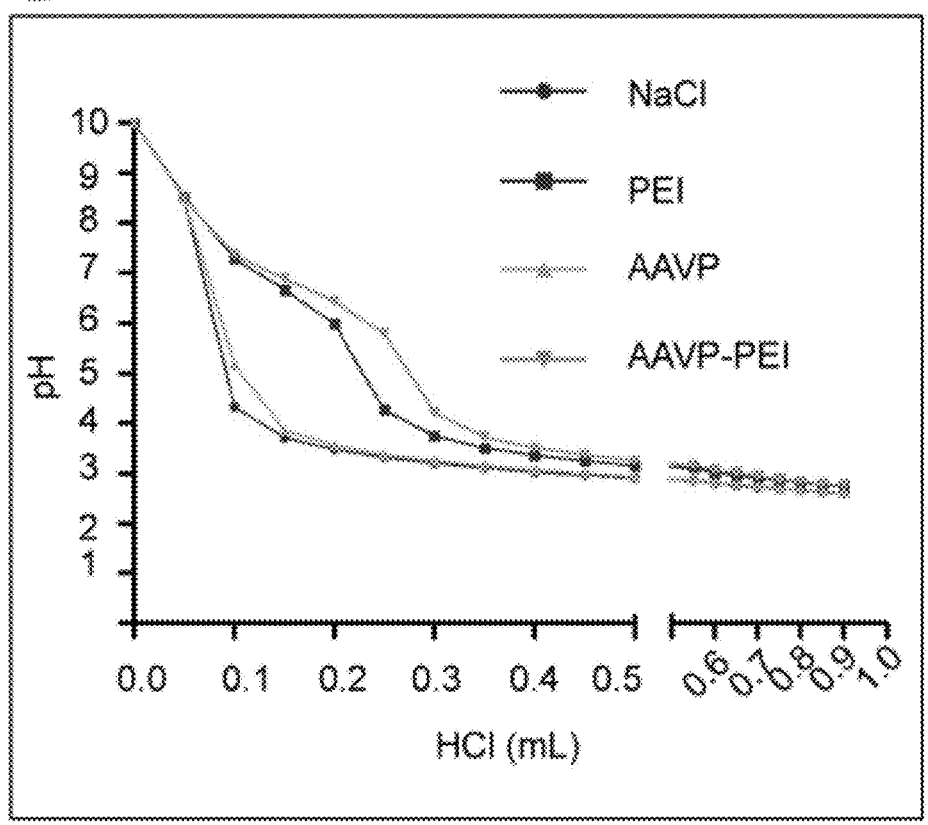
Figure 13A:
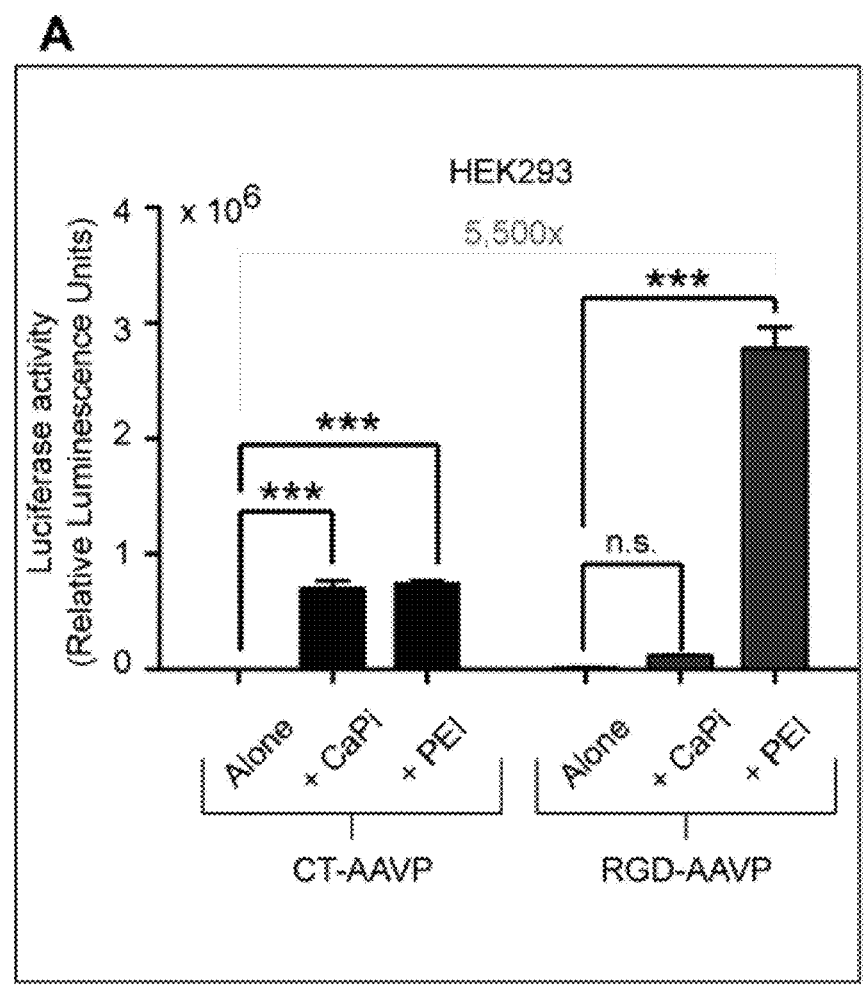
Figure 13B:
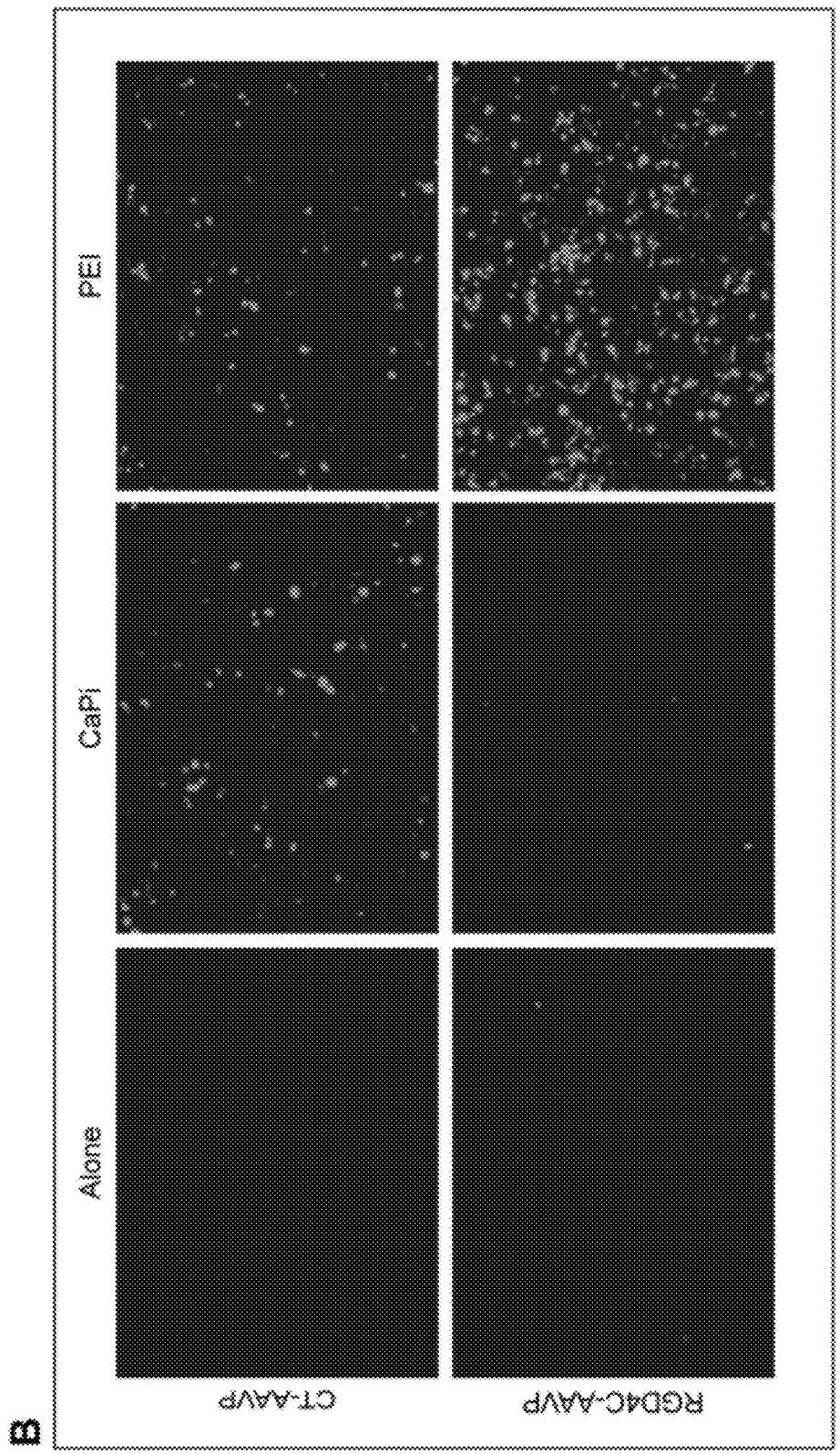
Figure 14A:
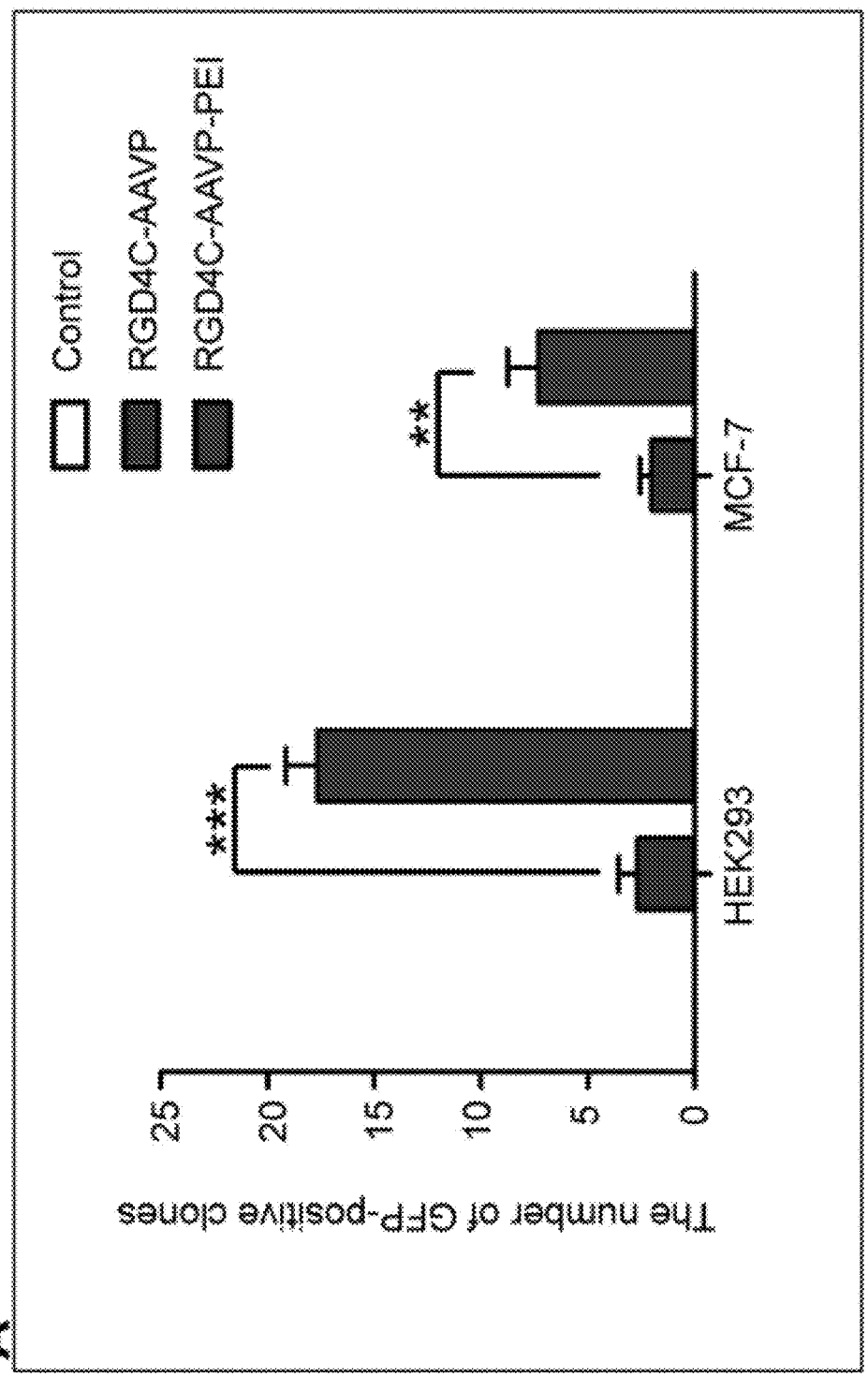
Figure 14B:
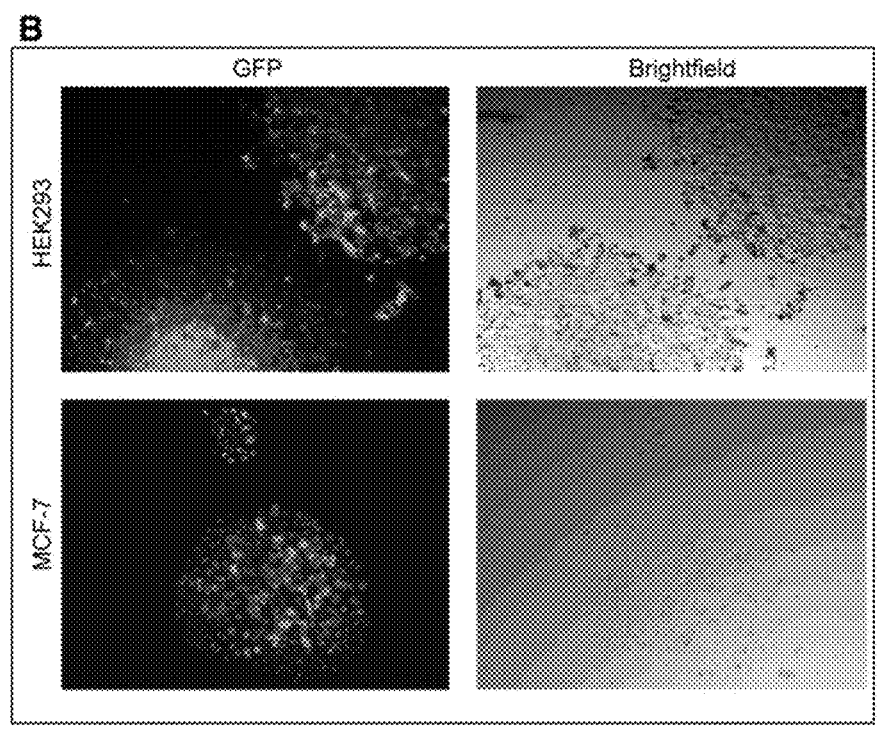
Figure 14C:
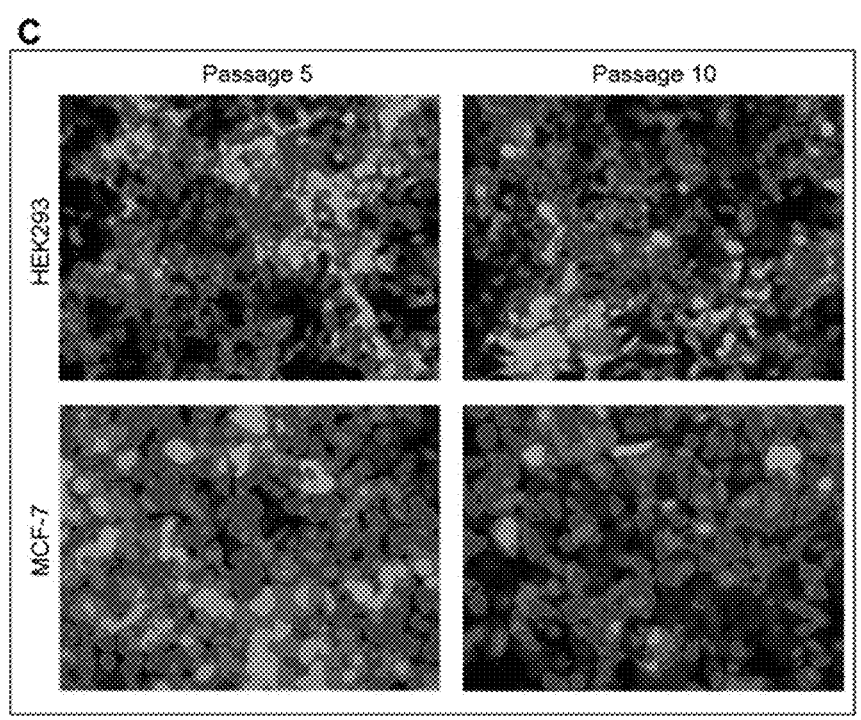
Figure 15A:
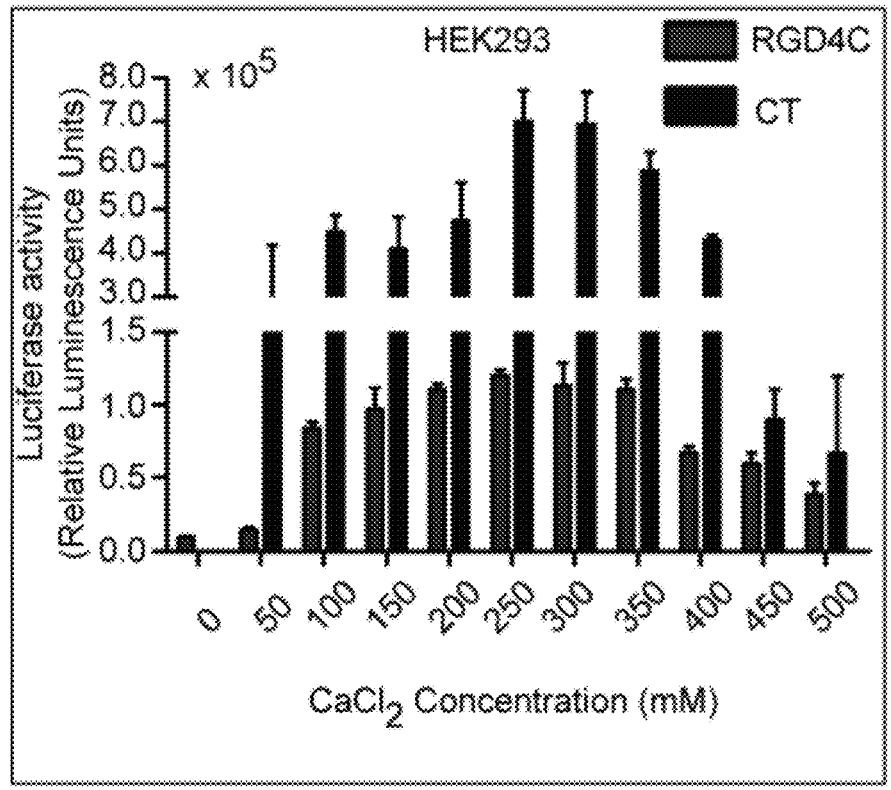
Figure 15B:
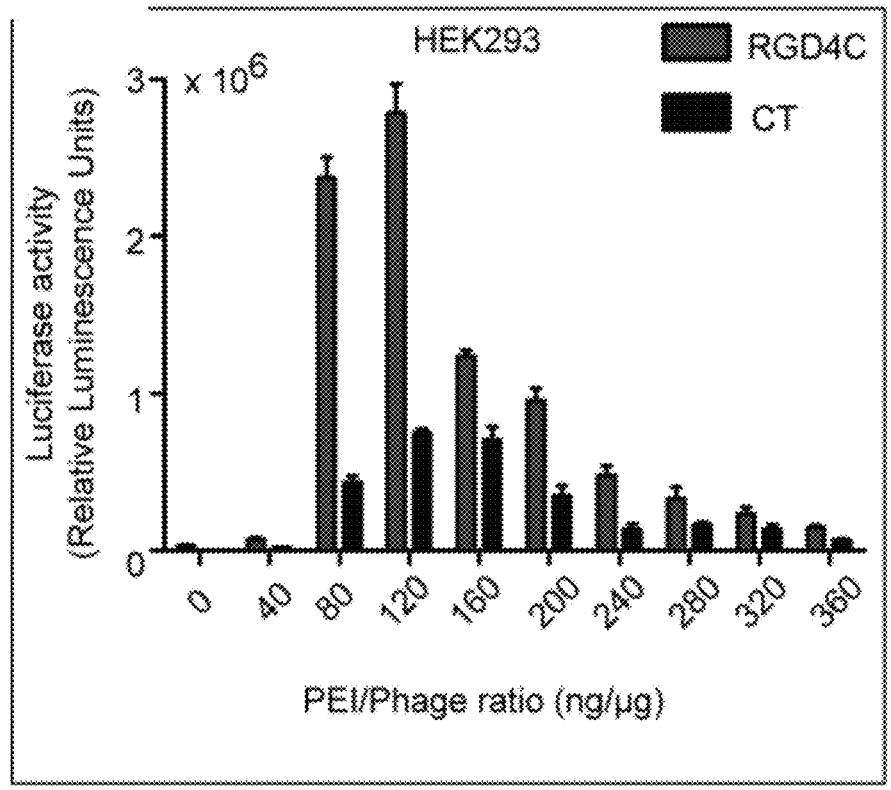
Figure 16:
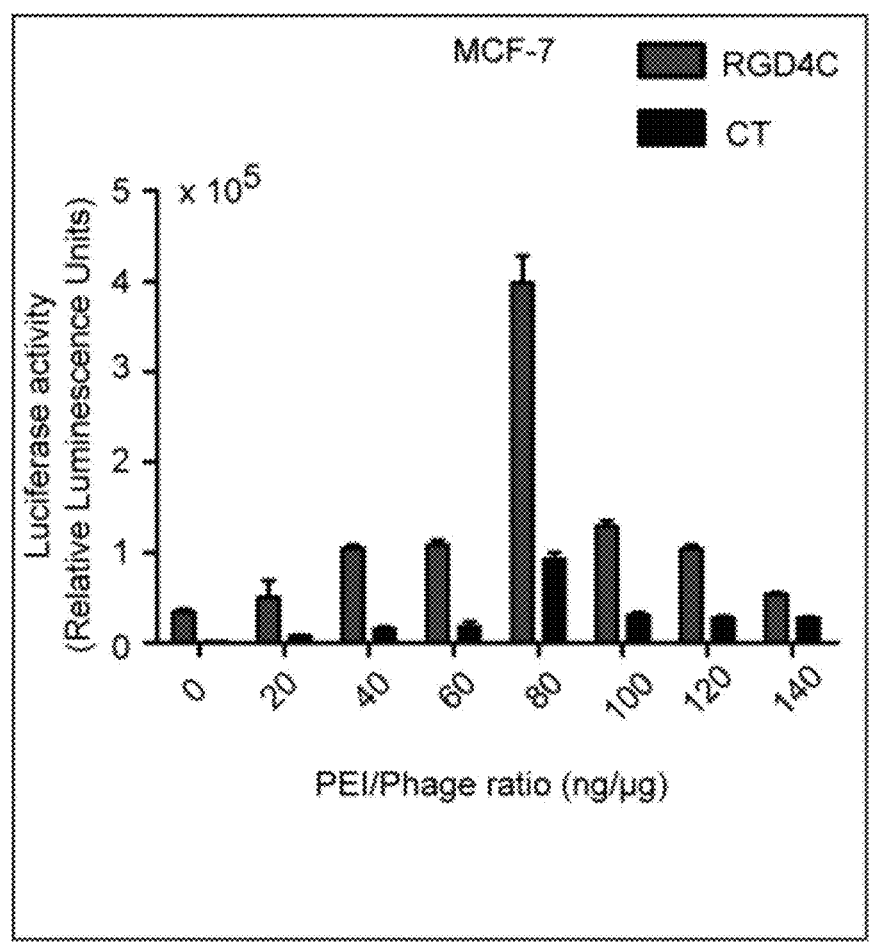

For a better understanding of the invention, and to show how embodiments of the same may be carried into effect, reference will now be made, by way of example, to the accompanying Figures, in which:

FIGS. 1A-1B shows schematic diagrams of one embodiment of a cationic bacteriophage/polymer hybrid according to the invention. FIG. 1a) shows negatively charged bacteriophage vectors being electrostatically assembled with cationic polymers to form hybrid bacteriophage/polymer complexes. A hybrid vector consists of the filamentous M13 bacteriophage and cationic polymer. The phage serves as a transgene carrier or vector displaying a tumour-targeting peptide on the phage capsid for entry into eukaryotic cells. The polymer counteracts the inherent negative charge of the phage particle. FIG. 1b) shows a recombinant filamentous bacteriophage with a genetically modified genome;

FIGS. 2A-2B shows the results of the characterization of mammalian cell transduction using the bacteriophage/polymer hybrid of the invention. FIG. 2a) shows optimization of polymer types and concentrations. M21 and 9 L cells were treated with RGD4C-phages carrying the Luc gene premixed with increasing concentration of poly-D-lysine (PDL) and DEAE.DEX, and Luc gene expression was measured using the luciferase assay at day 3 post-transduction. FIG. 2b) shows cytotoxicity of the RGD4C-phage complexed with increasing concentrations of cationic polymers in both M21 and 9 L cell lines. Cell viability was measured by using the CellTiter-Glo® cell viability assay, at 48 hr post transduction. The cell viability rate (%) was calculated as a percentage of control ($[A]_{test}/[A]_{control} \times 100$) (n=3);

FIGS. 3A-3C shows that the bacteriophage/polymer hybrid of the invention boosts gene transfer efficiency of the phage. FIG. 3a) shows the kinetics of Luc gene expression following transduction of M21 and 9 L cells with the RGD4C-phage premixed with PDL or DEAE.DEX (RGD4C-PDL and RGD4C-DEAE.DEX, respectively), RGD4C phage alone (RGD4C), and non-targeted phage (NT). The luciferase assay was performed daily over a time course of 5 days after vector transduction. FIG. 3b) shows that the number of GFP-positive cells in 9 L (top) and M21 (bottom) transduced by different vectors was quantified by FACS analysis. Gating was set to 10,000 total events in selected population. FIG. 3c) shows representative fluorescent images of 9 L cells at day 5 post transduction with different vectors as indicated;

FIGS. 4A-4D shows the results of the physico-chemical characterization of the bacteriophage/polymer hybrid of the invention. FIG. 4a) shows surface chemistry of bacteriophage vector. The ζ-potential of bacteriophage (bottom) was measured by zetasizer when varying phage titer (top) and pH (bottom). FIG. 4b) shows the effect of PDL and DEAE.DEX on phage particle size and ζ-potential. FIG. 4c) shows size distribution of the RGD4C-phage and RGD4C-phage complexed with polymers. FIG. 4d) shows morphology of the bacteriophage/polymer hybrid complexes and phage alone was analyzed using confocal microscopic imaging. Bacteriophage particles were immunofluorescence-stained using an anti-M13 phage primary antibody followed by a secondary goat anti-rabbit AlexaFluor-594 antibody;

FIGS. 5A-5C shows the results of the characterization of the cell transduction potential of the bacteriophage/polymer hybrid complex. FIG. 5a) shows that separate applications of polymer and phage on target cells have no effect on gene transfer by the bacteriophage. FIG. 5b) Depletion of phage particles from the supernatant of transduced cells. FIG. 5c) Confocal fluorescent microscopic images of 9 L cells following treatment with different vectors. Cells were first immunofluorescent-stained for extracellular phage using an anti-M13 phage primary and goat anti-rabbit AlexaFluor-594 secondary antibodies prior to permeablization and staining for intracellular phage using the same primary and goat anti-rabbit AlexaFluor-488 secondary antibodies;

FIGS. 6A-6C is an evaluation of the specificity of cell transduction by the targeted RGD4C-bacteriophage/polymer complexes. FIG. 6a) Targeted gene transfer to 9 L tumor cells by the RGD4C-phage/polymer was compared to that of either non-targeted phage/polymer or the mutant RGE4C/phage/polymer used as negative controls for targeting. FIG. 6b) Targeted gene transfer by the RGD4C-phage/polymer complexes was assessed in the normal $C_2C12$ myoblast cell line, using increasing concentrations of the PDL or DEAE.DEX cationic polymers. FIG. 6c) Expression of the $\alpha_v$ integrin receptor was investigated in 9 L tumor cells and $C_2C12$ myoblast cell line with anti-integrin primary and AlexasFluor-488 secondary antibodies;

FIGS. 7A-7B shows that hybrid phage/polymer complexes of the invention induce HSVtk/GCV-mediated cancer cell death. FIG. 7a) Morphological characteristics of 9 L cells following HSVtk/GCV (ganciclovir) therapy, as visualized with a bright field microscope. Confluent cells in the absence of GCV or cells treated with non-targeted phage and GCV show normal morphology. FIG. 7b) Evaluation of tumor cell killing by the RGD4C-phage/polymer complex, RGD4C-phage, and the non-targeted phage in 9 L cells in the absence or presence of GCV. Cell viability was determined by the CellTiter-Glo® cell viability assay;

FIG. 8 shows proposed mechanisms of hybrid bacteriophage/polymer vector cell transduction. Bacteriophage capsids interact with positively charged polymers to form complexes that are more "palatable" to the target cells. The resultant complexes retain a cationic charge and bind to the negatively charged cell membrane surfaces. Phage/polymer vectors are then internalized into cells via receptor-mediated endocytosis through specific interaction between the RGD4C ligand and $\alpha_v$ integrin receptors;

FIG. 9 shows the optimization of RGD4C-AAVP transfection of HEK293 cells using a luciferase assay. HEK293 cells were treated with increasing concentrations of RGD4C-AAVP carrying the Luc gene, ranging from 0 µg to 400 µg. Quantitative analysis of AAVP-mediated Luc gene expression was performed at day 3 post vector transduction. Results represent the average relative luminescence units (RLU) from triplicate wells and error bars represent standard error of the mean (s.e.m);

FIG. 10A-10F shows the characterization of chemical modified AAVP in HEK293 cells using a luficerase assay. Cells were transduced with CT-AAVP carrying the Luc gene with increasing concentrations of FIG. 10A) FUGENE® transfection reagent, FIG. 10B) LIPOFECTAMINE' transfection reagent, FIG. 10C) DOTAP, FIG. 10D) PEI, and FIG. 10E) calcium chloride. Luc gene expression was measured at day 3 post-transduction. FIG. 10F) Time course of luciferase gene expression over 5 days with AAVP alone (red) in combination with PEI (160 ng/µg, green), or with CaPi coprecipitation (300 mM $CaCl_2$), purple). Triplicate samples were obtained for each treatment. The entire experiment was repeated at least twice with similar results. Representative results are shown. Statistics were generated by one-way ANOVA, *, $p<0.05$, , $p<0.01$, *, $p<0.001$;

FIG. 11 shows that chemical modification of AAVP vectors enhances cell surface adsoption. Co-localisation of AAVP-PEI/CaPi and HEK293 cells was investigated by immunofluorescence staining. HEK293 cells were transduced with the optimised ratios of AAVP-CaPi, AAVP-PEI or AAVP alone. After 4 hr, cells were fixed and stained with rabbit anti-M13-phage primary antibody. Cells were counter stained, to detect phage particle with goat anti-rabbit Alexa Fluor-594 secondary antibodies (shown in red) and with DAPI (blue) to stain nuclei;

FIGS. 12A-12D relates to the mechanism by which PEI complexes and CaPi coprecipitates enhance AAVP-mediated gene transfer. 12A) Incubation time of the formation of complexes of AAVP with PEI or coprecipitates with CaPi. 12B) Depletion assay analysis of free cell-unbound AAVP particles from the supernatant of HEK293 cells transduced with CT-AAVP alone and in combination with either PEI or CaPi. Representative results demonstrating the percentage of cell binding (left) and photographs of colony counts of *E. Coli* cells. 12C) Flow cytometry analysis of HEK293 cells treated with CT-AAVP alone, a combination of either PEI or CaPi, and PBS solution (control). Fixation was conducted 4 hours post-treatment and immunofluorescence was performed as described in the materials and methods section. Representative results demonstrating the percentage of internalisation (left) and AAVP positive cell counts between AAVP alone (red) and AAVP coprecipitated with CaPi (blue). 12D) Acid-base titration curves for AAVP alone (pink), PEI (blue), AAVP-PEI (green), and blank (0.15M NaCl, red) solution from pH 10 to 3;

FIGS. 13A-13B shows that a combination of chemical and genetic modification boosts AAVP-mediated gene transfer. FIG. 13A) HEK293 cells were treated with targeted RGD4C-AAVP or CT-AAVP vectors, carrying the Luc reporter gene premixed with optimised ratios of either CaPi or PEI. Luc expression was analysed at day 3 post transduction. Results are representative of triplicate transductions of each treatment and the experiment was repeated twice. Statistics were generated by two way ANOVA, *, $p<0.05$, , $p<0.01$, *, $p<0.001$. FIG. 13B) Fluorescent imaging of HEK293 cells treated with AAVP vectors carrying the GFP reporter gene;

FIGS. 14A-14C shows the generation of HEK293 and MCF7 stable cell lines using RGD4C-AAVP-PEI complexes. HEK293 and MCF7 cells were treated with RGD4C-AAVP vectors, carrying the puro gene and GFP reporter gene, premixed with optimised PEI. Stably transduced cells were selected using puromycin resistance and grown in colonies. GFP positive cells, indicating stable transduction, were cultured through 5 to 10 passages. FIG. 14A) Colony counts to compare RGD4C-AAVP-PEI to control RGD4C-AAVP. FIG. 14B) Fluorescent images representing formation of GFP positive colonies. FIG. 14C) Fluorescent images of GFP positive stable cell lines at 5 and 10 passages;

FIGS. 15A-15B shows the optimisation of phage gene delivery efficacy following combination with chemical reagents. HEK293 cells were cultured in 48-well plates and treated with targeted phage displaying the RGD4C peptide or control phage (CT) without RGD4C. The phage carried a luciferase (Luc) gene expression cassette and was premixed with increasing ratios of the chemical reagents FIG. 15A) calcium phosphate and FIG. 15B) PEI, per phage as indicated in the figure. The luciferase activity was analysed at day 3 post phage transduction; and FIG. 16 shows the optimisation of phage/PEI cationic polymer complexes in the human MCF-7 breast cancer cell line. Cells were cultured in 48-well plates and treated with phage carrying the Luc gene expression cassette and premixed with increasing ratios of PEI per phage. Luciferase activity was analysed at day 3 post transduction.

EXAMPLES

The inventors investigated what they believe to be the first rate-limiting step of transgene transfer into a target cell by bacteriophages, i.e. the accessibility of the phage to the surface of the target cell and binding to its receptors to initiate cell entry, and subsequent transgene delivery. The inventors proposed that the efficiency of phage-mediated gene transfer would be improved if the phage is combined with a cationic polymeric system, which would improve the electrostatic binding of the phage to the negatively charged target cell membrane. The inventors also postulated that a cationic component would charge-associate with the phage capsid to switch the bacteriophage charge assisting its attachment to cell membranes, resulting in increased cell entry and enhanced gene transfer. They therefore converted the generally negative charge of a phage's capsid protein shell into a substantially positively charged surface.

As a proof of concept study, the inventors have provided examples (see below) of a novel hybrid vector targeted platform, i.e. a bacteriophage/cationic polymer hybrid. The invention comprises self-assembled complexes consisting of a recombinant M13 bacteriophage displaying the RGD4C-targeting ligand and containing a eukaryotic transgene cassette, coupled with a synthetic cationic polymer (see FIG. 1). The inventors have investigated the physico-chemical properties (surface chemistry, electrokinetic behaviour, size, morphology) and the biological activity (transgene expression, cytotoxicity, cell-vector interaction, and delivery mechanism) of the phage-polymer hybrids. The inventors were surprised to observe that the integration of a phage with a cationic polymer successfully generated positively-charged phage particles exhibiting an increased potential for binding to the surface of eukaryotic cells and a substantially improved gene transfer efficacy. Importantly, gene delivery by the hybrid vector remained targeted and specific, inducing complete targeted eradication of cancer cells.

Materials and Methods

Construction and Production of Bacteriophage Vectors

To generate bacteriophage-derived vectors for targeted gene delivery, the phage was genetically manipulated to (1) display copies of the RGD4C-tumor-homing peptide, on the pIII minor coat protein, and (2) carry a mammalian expression cassette encoding a cytomegalovirus (CMV) promoter-driven transgene. Phage viral particles were amplified, isolated and purified from the culture supernatant of host bacteria (*Esherichia coli* K91), according to the method of Hajitou et al., 2007 "Design and construction of targeted AAVP vectors for mammalian cell transduction". *Nat Protoc* 2, 523-531. Phage viruses were sterile-filtered through 0.45 µm filters, then titrated using a qNano particle analyzer (IZON Science Ltd. T.) based on a coulter technique also known as resistive pulse sensing.

Preparation of Hybrid Bacteriophage/Polymer Complexes

Cationic polymers, at a desired concentration, were added to phage vector preparations, mixed gently and incubated for 15 minutes at room temperature to form resultant bacteriophage/cationic polymer hybrid complexes of the invention. ζ-potential measurements were conducted using ZetaPALS (Brookhaven Instruments Corporation, NY, USA) based on electrophoresis in 1 mM KCl electrolyte solution. The pH dependency of ζ-potential was measured by changing the pH of the electrolyte solution through the titration of 0.1N HCl or NaOH. The size distribution was also evaluated using a qNano analyzer.

Cell Culture

Human Embryonic kidney (HEK293) cells were purchased from American Type Culture Collection (ATCC) and the human MCF-7 breast cancer cells were from Cancer Research UK. Human M21 melanoma cells were provided by Dr David Cheresh (University of California, La Jolla). Rat 9 L glioblastoma cells were a gift from Dr Hrvoje Miletic (University of Bergen, Norway). The mouse $C_2C12$ myoblast cell line was provided by Dr Francesco Muntoni (University College London, UK). All cell lines were maintained in a humidified atmosphere of 37° C. in a 5% $CO_2$ and cultured in Dulbecco's Modified Eagle's Medium (DMEM, Sigma) supplemented with 10% Fetal Bovine Serum (FBS, Sigma), Penicillin (100 units/ml, Sigma), Streptomycin (100 µg/ml, Sigma) and L-Glutamine (2 mM, Sigma). The $C_2C12$ cells were grown in 20% FBS (fetal bovine serum). The cells were passaged every 3 to 4 days, when they were 70 to 80% confluent.

In Vitro Cell Transduction by Phage-Derived Vectors

Cells were seeded into 48-well plates and grown for 48 hours to reach 60%-80% confluence. The phage/polymer hybrid complexes, prepared at optimal ratios, or the phage vector alone (as control), were applied to cells in serum-free media, followed by 4 hours incubation at 37° C. The medium was then replaced with fresh serum-containing medium and the cells were then incubated at 37° C. to allow transgene expression.

Typically, CT-AAVP served as negative controls. GFP expression was examined using a Nikon Eclipse TE2000-S fluorescence microscope that has a fitted Nikon digital camera (DXM1200F). Determination of cell transduction efficacy by the phage vectors was performed by using a phage carrying the firefly luciferase (Luc) and the green fluorescent protein (GFP) reporter transgenes. Luciferase reporter gene expression in transduced cells was determined with the Promega Steady-glo® luciferase assay kit, according to the manufacturer's protocol, it was then quantified using a Promega plate reader, and normalized to 100 µg protein levels as determined by the Bradford assay. GFP expression was monitored daily by using a Nikon Eclipse TE2000-U fluorescence microscope. 5 days post transduction, the cells were harvested and GFP positive cells were counted using a FACS flow cytometer (BD Biosciences, USA) by a standard gating technique. Cell viability was determined by CellTiter-Glo® cell viability assay kit according to the manufacturer's protocol, and quantified using a Promega plate reader. All experiments were performed in triplicate.

Determination of Tumour Cell Killing In Vitro

9 L cells were seeded in a 48-well plate and incubated for 48 hours, to reach 60%-80% confluence. Next, cells were transduced with the hybrid complex or phage vector alone (as control) carrying the Herpes simplex virus thymidine kinase (HSVtk) gene. GCV was added to the cells (10 µM) at day 3 post vector transduction and renewed daily. Viable cells were monitored under a microscope and cell viability was measured at day 5 post GCV treatment by using the CellTiter-Glo® cell viability assay kit.

Confocal Microscopy

HEK 293 cells were seeded on 18 $mm^2$ coverslips in 12-well plates. HEK293 cells were incubated with CT-AAVP vectors, complexed with optimised ratios of transduction supporting reagents. CT-AAVP alone was used as a negative control. After a 4 hr incubation, HEK 293 cells, at approximately 50-60% confluence, were washed with phosphate buffered saline (PBS) and fixed in 4% paraformaldehyde (PFA), 250 mM HEPES buffer for 10 to 15 min at room temperature to stain for $α_v$ integrins. For phage staining, cells were incubated with phage vectors for 4 hr at 37° C., followed by washing with PBS and fixation with 4% PFA. Following fixation, the cells were then treated for 5 minutes with 50 mM Ammonium Chloride to quench free aldehyde groups from fixation, permeabilized with 0.2% Triton X-100 (Sigma), washed, and blocked with PBS containing 2% bovine serum albumin (BSA). Next, the cells were incubated with the primary antibodies: rabbit anti-$α_v$ integrin (diluted 1:50), rabbit anti-M13 bacteriophage (1:1000, Sigma) for 1 hour, then with secondary AlexaFluor-conjugated antibodies (diluted 1:750 in 1% BSA-PBS, Invitrogen) with/without 4',6-diamidino-2-phenylindole (DAPI) (diluted 1:2000 in 1% BSA) for 1 hour at room temperature. Finally, the cells were mounted, in the presence of DAPI, in Mowiol mounting medium (prepared in-house). Images were acquired with a Leica SP5 confocal microscope.

In Vitro-Depletion Assay

HEK293 cells were seeded at a density of 5×104 cells/well in 48-well plates and allowed to grow until 70-80% confluent followed by treatment with AAVP prepared to optimal ratios. The plates were placed on ice for 1 hr to prevent AAVP internalisation. Supernatants were extracted and serially diluted in 1×PBS. The number of AAVP particles was quantified using the K91 Kan bacterial infection method and counting transducing units, as previously reported [11].

Flow Cytometry

HEK293 cells were seeded at a density of $1×10^5$ cells/well in 12-well plates and grown until 70-80% confluent. Cells were then treated with AAVP-CaPi coprecipitates, AAVP-PEI or AAVP alone and incubated for 2 hr at 37° C. Endocytosis was stopped by placing the cells on ice followed by 3 washes with PBS to remove unbound phage. The cells were then trypinised for 5 minutes to remove surface bound phage and pelleted by centrifugation at 200 rpm for 5 min followed by fixation in 4% paraformaldehyde (PFA) for 10 min at room temperature. To examine AAVP internalisation, cells were blocked with 0.1% saponin in 2% BSA-PBS for 30 minutes. Cells were then incubated with rabbit anti-M13-phage antibody (diluted 1:1000) in 0.1% saponin in 1% BSA-PBS for 1 hr at room temperature. Cells pellets were washed by being resuspended in 0.1% saponin in 1% BSA-PBS followed by centrifugation three times and then incubated with goat anti-rabbit AlexaFluor-647 (diluted 1:500) in darkness for 1 hr at room temp. Finally cells were washed twice with 0.1% saponin-PBS and resuspended in PBS before analysis.

FACS analysis was performed using a BD FACscalibur Flow cytometer (BD Biosciences) equipped with an argon-ion laser (488 nm) and red-diode laser (635 nm) the mean fluorescence intensity was measured for at least 10,000 gated cells per triplicate well. Results were analysed using Flojo (TreeStar) software.

Endosome Buffering Capacity Measurements

The acid-base titration method was used to determine the endosome buffering capacities of the AAVP-PEI prepared to their optimised ratios in sterile water to a total of 20 ml and the pH adjusted to pH10 by sodium hydroxide solution (NaOH). Subsequent additions of hydrogen chloride solution (HCl) were used to titrate the solution to pH3 while changes in pH were recorded using a pH meter. Titrations of sodium chloride solution (NaCl), polymer solution and AAVP solutions were used as controls. The natural endosome pH range 7.4-5.1, was used to calculate the endosome buffering capacity of the AAVP/polymer complexes.

Statistical Analysis

Statistical analyses were performed by using GraphPad Prism software (version 5.0). Error bars represent standard error of the mean (s.e.m). P values were generated by ANOVA and denoted as follows: *$p<0.05$, $p<0.01$ and *$p<0.001$.

Example 1—Amalgamation of Phage With Cationic Polymers Boosts Gene Transfer to Mammalian Cells by Phage-Based Vectors The inventors assessed whether the efficiency of transgene delivery by the RGD4C-phage to eukaryotic cells can be improved if phage viral particles are integrated with cationic polymers. The inventors therefore studied the efficacy with which the RGD4C-phage/polymer complexes according to the invention (see FIG. 1) transduce Human M21 melanoma cells, which are known to express high levels of the $\alpha_v$ integrin receptors for the RGD4C ligand. To rule out the possibility that the observed effects are not cell or species specific, the inventors also assessed the efficacy of the new phage product on rat 9 L glioblastoma cells, which have previously been shown to be transduced by the RGD4C-phage. The inventors first sought to determine the optimal ratio of the cationic polymer to the RGD4C-phage by keeping the latter fixed at $10^5$ particles per cell, and adding increasing concentrations of the polymer using the RGD4C-phage vector carrying luciferase (Luc) reporter gene. The inventors also assessed the suitability of various cationic polymers, such as poly-D-lysine (PDL), diethylaminoethyl-dextran (DEAE.DEX), polyethyleneimine (PEI), polybrene and protamine sulfate. Quantification of luciferase activity in M21 and 9 L cells at 72 hr post cell transduction showed that Luc gene expression by the RGD4C-phage dramatically improved with increased concentrations of PDL and DEAE.DEX polymers, as shown in FIG. 2a, as compared to the RGD4C-phage alone (0 µg/ml of polymer). Maximum gene transfer levels were achieved in both M21 and 9 L cells at polymer concentrations of 7 µg/ml for PDL and 15 µg/ml for DEAE.DEX, respectively, after which a gradual decrease in Luc gene expression occurred (see FIG. 2a). To determine whether the decreased transgene expression at high ratios of the cationic polymers was associated with PDL and DEAE.DEX cytotoxicity, the inventors performed cell viability assays and showed that this range of polymer concentrations was not associated with any such toxic effect (see FIG. 2b).

Next, the inventors used the optimal concentrations of PDL and DEAE.DEX polymers to assess the efficacy of gene transfer by the hybrid RGD4C-phage/polymer complex over a period of 5 days following transduction of M21 and 9 L cells (see FIG. 3a). Four different vector systems were investigated: non-targeted phage (NT), targeted RGD4C-phage (RGD4C) displaying the tumour-targeting ligand on pIII minor coat protein, RGD4C-phage complexed with PDL (RGD4C-PDL), and RGD4C-phage complexed with DEAE.DEX (RGD4C-DEAE.DEX). A considerable increase in expression of the Luc transgene was detected in both M21 and 9 L cells transduced with the hybrid RGD4C-PDL and RGD4C-DEAE.DEX phage/polymer complexes, as shown in FIG. 3a. Luc gene expression increased rapidly over time, while luc gene expression remained low in cells transduced by the RGD4C phage alone, and no luc gene expression was detected in cells incubated with a control non-targeted phage.

To explore the superiority of the RGD4C-phage vector combined with cationic polymers, the inventors used a phage carrying the GFP reporter transgene. At day 5 post transduction, fluorescence-activated cell sorting (FACS) analyses and microscopic imaging of M21 and 9 L cells revealed a dramatic increase in GFP expression in those treated with phage/polymer complex (as shown in FIGS. 3b, c). No GFP expression was detected in the cells treated with the control non-targeted phage. These data confirm that the integration of a cationic polymer with a bacteriophage significantly boosts gene transfer efficacy.

Example 2—Physical Characterization of the Hybrid Phage/Polymer Complexes

To gain an insight into the mechanism of the improved gene transfer by the hybrid phage/polymer complexes illustrated in Example 1, the inventors explored the electrostatic charge on the phage capsid. The inventors first investigated the charge characteristics of the bacteriophage viral particles by measuring their ζ-potential using electrophoresis (see FIG. 4a). They found that the bacteriophage is negatively charged at a physiological pH. The data indicate that the RGD4C-phage possesses an acidic surface, with an isoelectric point of pH=3 as determined from ζ-potential=f(pH). Next, the inventors analyzed the ζ-potential of the bacteriophage vectors following hybridization with cationic polymers PDL and DEAE.DEX (see FIG. 4b). The inventors found that this potential shifts from a negative value, for unmodified bacteriophage, to a positive value, for the phage complexed with polymers. This strongly suggests that the polymer modifies the electrostatic charge of the bacteriophage with which it associates. This increase in the ζ-potential can be attributed to surface adsorption of the polymer counteracting the inherent negative charge of the bacteriophage particles.

In order to prove the hypothesis that cationic polymers lead to aggregation of the phage viruses resulting in the formation of larger particles, the inventors conducted a second set of experiments. Size measurements of phage/PDL complexes at the optimal polymer concentration (7 µg/ml), revealed the average diameter of the particles to be 7-times greater than the phage alone, as shown in FIGS. 4b, 4c. Moreover, the size distribution shows that the self-assembly of the RGD4C-phage and the cationic polymers yields a monodisperse product (see FIG. 4c). The inventors also examined the appearance of the phage/polymer complexes by confocal microscopy. As shown in FIG. 4d, single particles of the filamentous phage morphology were observed in uncomplexed phage, while two morphologies were observed when the phages were mixed with a PDL polymer. These consisted either of complex species containing a number of the phage particles, or the individual phage viral particles.

Example 3—Investigation of the Phage/Polymer Cell Accessibility and Entry

To gain further insight into the improved gene delivery efficacy by phage/polymer complexes, the inventors investigated whether complex formation was required prior to treatment of cells. 9 L cells were therefore treated with the cationic polymers alone for 30 minutes, followed by removal of excess polymer and washing, before addition of the RGD4C-phage. The inventors found that separate application of the cationic polymers followed by the RGD4C-phage had no significant effect on gene delivery efficacy compared to that of the pre-formed phage/polymer complex (see FIG. 5a). These data suggest that a pre-incubation of the phage with the polymer is required for the active formation of the phage/polymer hybrid complex according to the invention.

The inventors also determined whether gene delivery efficiency by the RGD4C-phage is limited by inefficient access and binding to the surface of cells. The inventors carried out a supernatant-depletion assay, where the free cell-unbound phage in the external fluid phase above the adherent cell layer was quantified by infection of host bacteria followed by colony counting. A large amount of free the phage (90% of input phage particles) was recovered from the supernatant of the cells that were treated with the RGD4C-phage vector (see FIG. 5b), showing that only a small fraction (10% of input phage) was bound to the cell surface. By contrast, very little of the phage (6%) was recovered from the supernatant of cells that were incubated with the RGD4C-phage/polymer complex, indicating that most of the RGD4C-phage (94%) was bound to the surface of cells. No phage depletion was observed in the supernatant of cells treated with the control non-targeted phage. Confocal microscopic imaging, following immunofluorescence with an anti-phage antibody, revealed greater cell surface binding in cells treated with the phage/polymer complex than in those incubated with the uncomplexed phage. No phage was observed on cells incubated with the control non-targeted phage (see FIG. 5c). These data strongly suggest that modification of the phage capsid charge by incorporation into a cationic complex does indeed increase phage binding to the cell surface and also helps to overcome the extracellular accessibility barrier due to electrostatic repulsion.

Example 4—The Phage/Polymer Hybrid Complexes Retain Targeting and Specificity of Gene Transfer The inventors confirmed that the targeting properties of the RGD4C-phage vector remain intact in the phage/polymer complex and that transduction of cells is specific and mediated by binding of the RGD4C ligand to the $\alpha_v$ integrin receptors. Cell transduction efficiency of the RGD4C-phage/polymer complex was compared to that of complexes between the polymer and either the non-targeted phage or the phage displaying a mutant version of RGD4C (RGE4C, D-E). As shown in FIG. 6a, Luc gene expression in cells treated with the RGE4C-phage/polymer complex was non-significant and comparable to that of the non-targeted phage/polymer complex. Next, to confirm the ability of the RGD4C-phage/polymer complexes to target gene delivery to tumors cells specifically, but not to normal cells lacking the $\alpha_v$ integrin receptors, the inventors compared the transduction efficiency of the 9 L tumor cells and the normal $C_2C12$ myoblast mouse cell line using the RGD4C-phage mixed with increasing concentrations of either PDL or DEAE.DEX cationic polymers. While the RGD4C-phage/polymer complexes reproduced the expected pattern of Luc transgene expression in 9 L cells, no transgene expression was induced in $C_2C12$ cells by any ratio of both the RGD4C/phage and either PDL or DEAE.DEX polymers, as shown in FIG. 6b. Finally, the inventors confirmed expression of the $\alpha_v$ integrin receptors on the 9 L tumor cells; in contrast, the $C_2C12$ myoblast mouse cell-line do not express this integrin (see FIG. 6c). These findings confirm that gene delivery by the RGD4C-phage/polymer hybrid complex is targeted, specific and dependent on $\alpha_v$ integrin receptors.

Example 5—Enhancement of the HSVtk Ganciclovir (GCV)-Mediated Cell Death by Hybrid Bacteriophage/Polymer Complex After establishing that integration of cationic polymers with bacteriophage vectors substantially increases gene transfer efficacy, as described above, the inventors then assessed the effect of the polymers on a specific clinical application of phage, namely gene therapy. To test the efficacy of tumor cell killing of the RGD4C-phage/polymer complex, the inventors constructed a RGD4C-phage vector carrying the Herpes simplex virus thymidine kinase (HSVtk) gene, acting as transgene. When combined with the GCV pro-drug, this gene can serve as a suicide gene. The inventors chose to conduct their experiments in the 9 L glioblastoma model as this tumor type is highly aggressive and remains a major clinical challenge. The inventors compared the RGD4C-phage vector alone (as control) with the RGD4C-phage/polymer complex according to the invention. The HSVtk suicide gene therapy was induced at day 3 post-transduction by daily treatment with GCV for 5 days. Morphological characteristics of the 9 L cells 3 days post GCV treatment was visualized by brightfield microscopy. FIG. 7a shows normal morphology of confluent cells in all treatments, in the absence of GCV, and in cells treated with a combination of the non-targeted phage and GCV. There was a dramatic increase in the number of cells that detached from the substrate by the RGD4C/phage-polymer, upon GCV treatment, as compared to the uncomplexed RGD4C-phage. At day 5 post GCV treatment, a cell viability assay (see FIG. 7b) revealed 75% cell death in the cells that had been transduced with the uncomplexed RGD4C-phage, but a complete eradication of tumor cells by the RGD4C/phage complexed with either PDL or DEAE-DEX polymer. No cell death was detected in the absence of GCV, or in cells that had been treated with the non-targeted phage. These findings clearly establish that combining the bacteriophage with a cationic polymer greatly increase its potential as a gene therapy vector.

Example 6—Transfection Reagents Enhance AAVP-Mediated Gene Transfer in HEK293 Cells When transducing cells, a relatively high titre of RGD4C-AAVP (up to $1 \times 10^6$ particles per cell) is required (see FIG. 9). The relatively low transduction efficiency of these vectors could result, at least partially, from the capacity of receptors that are targeted by the AAVP. The number of cell surface receptors and their availability determine the homing efficiency of targeting compound. The inventors found that transduction efficiency of increasing amounts of RGD4C-AAVP does not increase in a concentration-dependent manner but instead led to saturation of gene expression of 25 mg AAVP at approximately $1.5 \times 10^5$ RLU or 300-fold over CT-AAVP vector. This phenomenon limits efficient transgene delivery mediated by AAVP.

In order to determine whether transgene expression could be improved by chemical modification, transduction supporting agents were premixed with a CT-AAVP vector carrying the Luc gene. Analysis of luciferase expression at day 3 post-transduction revealed that Luc expression dramatically improved with increased concentrations of reagents compared to CT-AAVP alone (see FIG. 10). Transfecting HEK293 cells with mixtures of CT-AAVP and lipid-based reagents enhanced in vitro Luc expression in a dose-dependent manner (see FIG. 10A to 10C). At maximal levels of Luc expression, FUGENE® transfection reagent, at 1 μl/μg, improved transgene expression by 70-fold; LIPOFECTAMINE' transfection reagent (see FIG. 10A), at 1 μl/μg, increased transgene expression by 80-fold (see FIG. 10B); DOTAP, at 4,200 ng/μg, augmented transgene expression by 20-fold (see FIG. 10C). For the cationic polymer, PEI, and CaPi (see FIGS. 10D and 10E, respectively), Luc expression increased with increasing concentrations of reagents reaching a maximum at 160 ng/μg for PEI and 300 mM for $CaCl_2$), followed by a gradual decrease. At the optimal ratio, no overt cytotoxicity was detected using light microscopy and cell viability assays (data not shown). The reagents PEI and CaPi elicited higher transduction efficiencies compared to the lipid-based reagents reaching 1,300 to 1,400-fold compared to 20 to 80-fold. Therefore, PEI and CaPi were selected for further studies of AAVP-mediated gene delivery.

Next, the inventors used the optimal ratios of PEI and CaPi to assess the efficacy of gene transfer by the AAVP over a period of 5 days following transfection of HEK293 cells (see FIG. 10F). A significant increase in Luc expression was detected in cells transduced with AAVP-PEI and AAVP-CaPi which increased rapidly over the time course compared to CT-AAVP alone, which elicited barely detectable levels of gene expression. PEI and CaPi were therefore selected for subsequent studies to determine the underlining mechanisms of transduction mediated by chemically modified AAVP vectors.

Example 7—Mechanism by Which PEI Complexes and CaPi Coprecipitates Enhance AAVP-Mediated Gene Transfer CaPi and PEI Facilitates Interaction Between Virus and Cell Membrane The lack of binding to the cell surface is an important factor limiting AAVP-mediated gene transfer. Previous investigation has established an essential role of the RGD4C ligand, displayed on AAVP capsid, for binding and uptake into mammalian cells in vitro. Therefore, the inventors further tested the hypothesis that the enhanced efficacy of gene transfer by coprecipitated AAVP vectors is likely due to effects on virus adsorption to target cell membranes and increased internalisation.

HEK293 cells were treated with CT-AAVP premixed with optimised concentrations of PEI and CaPi and compared to CT-AAVP alone (see FIG. 11). Immunofluorescence imaging using anti-M13 phage staining (red) revealed that AAVP-CaPi precipitates and AAVP-PEI complexes co-localise with the cell surface membranes indicating increased cell adsorption compared to control CT-AAVP alone in which no co-precipitates or complexes were observed.

This result was quantified by performing a supernatant-depletion assay, in which the amount of free cell-unbound AAVP particles in the external aqueous phase is counted through infection of host bacteria and colony analysis. In HEK293 cells treated with AAVP alone, 100% of free unbound AAVP was recovered from the supernatant, in contrast to only 9% AAVP being recovered from the supernatant of cells treated with AAVP vectors coprecipitated with CaPi and vectors complexed with PEI, indicating that the majority of the AAVP-CaPi and AAVP-PEI was bound to the surface of cells (see FIG. 12B). These data strongly suggest that the integration of AAVP with CaPi or PEI into complexes mediates gene transfer in to mammalian cells, at least in part, by allowing AAVP binding to the cell surface and overcoming the extracellular accessibility barrier.

Next, the inventors set out to determine if there was increased cellular uptake of AAVPs following chemical modification with CaPi and PEI using HEK293 cells. An AAVP internalization assay was performed by which intracellular AAVPs were stained followed by flow cytometry quantification. The addition of PET and CaPi co-precipitate allowed for an increase in AAVP internalisation, as indicted by the higher intracellular AAVP signal as well as enhanced AAVP counts/10,000 cells (see FIG. 12C). These results thus highlight the accumulation of internalized AAVP within intracellular compartments.

Buffering Capacity

Endosomal escape is an important factor to be considered for the design of gene delivery vectors. This mechanism is associated with the buffering capacity of gene vectors within the pH range of 7.4 to 5.0, in which vectors traffic from the extracellular environment into acidified endosomal compartments. Polycations with high buffering capacity can mediate efficient escape from the endosome to the cytosol triggered by the acidic endosome via a mechanism termed 'Proton sponge effect'. The endosomal-lysosomal pathway has been identified as an intracellular barrier to AAVP particles, which are sequestered and degraded within the acidic environment, reducing their ability to deliver DNA into the nucleus. Previously, it was reported that cationic polymers such as PEI increase the gene transfer efficiency of non-viral vectors due to their ability to induce endosomal escape. Therefore, the inventors investigated whether there was a potential second mechanism, apart from increased surface adsorption, contributing to the increased gene transfer delivery of the AAVP-PEI. To assess whether our AAVP-PEI possess this property acid-base titrations were performed to compare AAVP alone, PEI alone and the AAVP-PEI with the control sodium chloride (NaCl) solution (see FIG. 12D). The AAVP-PEI complex elicited a buffering capacity similar to PEI polymer alone, and required ~0.2 ml HCl extra compared to control NaCl to lower the pH from 7.4 to 5.1 (see FIG. 12D). AAVP in the absence of PEI displayed a titration curve similar to NaCl and therefore has no buffering capacity without the presence of the polymer.

Example 8—Combined Genetic and Chemical Modifications Further Enhances Gene Transfer of AAVP Having shown that chemical modification of AAVP vectors with CaPi and PEI polymer increases gene delivery efficiency; the inventors next sought to determine whether incorporation of genetic targeting into the vector complexes would lead to further enhancement. AAVP vectors were originally developed to target mammalian cells for targeted cancer gene therapy applications. The targeting peptide ligand, cyclic RGD4C, was engineered to be displayed on the minor coat protein PIII thus allowing the vector (RGD4C-AAVP) to enter mammalian cells expressing $\alpha_v$ integrin receptors, highly expressed on cancer cells. Therefore, the inventors investigated the effect of integration of increasing concentrations of $CaCl_2$ and the cationic polymer PEI with targeted RGD4C-AAVP vectors, carrying the Luc reporter gene, in HEK293 cells (see FIG. 15). HEK293 cells were chosen as they display $\alpha_v$ integrins and have previously been used for investigation of targeted RGD4C-AAVP.

The efficacy of gene transfer of the AAVP vectors, with either CaPi or PEI was assessed using the optimized ratios of each transfection reagent. HEK293 cells treated with the targeted RGD4C-AAVP vector revealed that only PEI significantly increased gene expression when compared to CT-AAVP alone and resulted in increases of 5,500 fold (see FIG. 13). CaPi did not result in a significant increase when coprecipitated with targeted RGD4C-AAVP (see FIG. 13A). FIG. 13B provides representative data of the CT-AAVP and RGD4C-AAVP, carrying the GFP reporter gene, and further highlights the superiority of the AAVP vectors when complexed with PEI or coprecipitated with CaPi.

These data clearly demonstrate that the cationic polymer PEI with the incorporation of the targeting ligand provides the highest efficacy for AAVP-mediated transduction. Therefore, the combination of RGD4C-AAVP with PEI was selected for transduction of the MCF-7 breast cancer cell line (see FIG. 16).

Example 9—Application: Stable Cell-Line Production

Having shown that the combination of both chemical and genetic modifications of AAVP vectors greatly enhance gene transfer efficiency we finally attempted to establish how our novel RGD4C-AAVP-PEI complex could be utilized in scientific research. The inventors aimed to determine the efficacy of transgene expression mediated by RGD4C-AAVP-PEI complex by using it for stable cell-line production. To demonstrate that the novel vector system is not specific to a particular cell-line, the inventors decided to transduce the human MCF-7 cell-line as well as the HEK293 cells. HEK293 and MCF-7 cells were transduced with RGD4C-AAVP-PEI vectors, carrying the GFP reporter gene and the puro gene to produce stably transduced cell-lines, by using puromycin resistance to isolate clones (see FIG. 14). The combination of PEI with the RGD4C-AAVP significantly increased the number of clones obtained compared to CT-AAVP-PEI complexes (see FIG. 14A). Once clones were isolated by puromycin resistance they were split, cultured and passaged. FIG. 14C presents the successful production of a HEK293 and MCF7 stable cell-lines, in which GFP positive cells are maintained through 5 to 10 passages. Stable cell-line production is possible with the AAVP vector as the AAV genome bestows long term transgene expression in episomal form once in the nucleus.

Discussion

Despite some attractive features, bacteriophage viruses are still considered poor vectors for gene transfer, and this limits their application in a broad range of disciplines, such as nanotechnology, biology and medicine. However, the inventors have previously reported that phage gene transfer efficacy can be improved by combining bacteriophages with the attributes of animal viruses. This was demonstrated by the incorporation of the genetic cis-elements (ITRs) from the animal virus AAV-2 into the phage genome, resulting in an altered transgene cassette and subsequent enhanced gene delivery efficacy. Such genetic improvements only become relevant following transfer of the genome to the nucleus. Therefore, the attachment, entry, and intracellular trafficking of the vector remain rate-limiting. The first, and arguably the most important of these steps is the binding of the vector to the target cell surface, prior to internalization and the transport of its genetic load to the nucleus. The inventors have now shown a highly effective way to improve this initial rate-limiting step of phage binding. One factor that seems to impede binding to cells is the electrostatic repulsion between the negative charges normally carried by both the phage and the cell membrane. The inventors have counteracted this by complexing their improved phage with a cationic polymer. This novel bacteriophage-derived vector platform is thus based on a combination of genetic and chemical modifications.

The inventors have shown that the addition of certain types of cationic polymers to genetically modified phages at an appropriate ratio leads to the formation of self-assembled complexes that can greatly improve transgene expression. The transduction of mammalian cells by such phage/polymer complexes remains specific and targeted and occurs through the binding of the RGD4C ligand to avintegrin receptors. A pre-incubation and aggregation step seems to be important. Decreased transgene expression is observed at very high polymer concentrations but this is not related to any detectable cytotoxic activity; it might be due to the formation of larger aggregates that reduce the efficacy of cellular internalization.

The inventors have confirmed that the affinity of the uncomplexed phage vector for the cell surface is weakened by an electrostatic effect. The negatively-charged amino acid residues (Glu2, Asp4, and Asp5) of the major coat protein pVIII are responsible for an overall large negative charge on the uncomplexed phage viral particles, which are consequently repelled to some extent by the similar charge on the cell membranes of target cells. However, the addition of the positively-charged polymer successfully counteracts this, imparting an overall positive charge that greatly improves vector-cell binding (see FIG. 8).

The inventors have also demonstrated the potential of this newly developed phage-polymer vector for clinical applications. It significantly improves the transfer of the suicide HSVtk gene, which is used in conjunction with the prodrug GCV for cancer gene therapy. The enzyme, thymidine kinase, phosphorylates the prodrug GCV to GCV monophosphate, which is then further phosphorylated to the cytotoxic GCV triphosphate, leading to programmed cell death via the inhibition of DNA polymerase. HSVtk gene transfer using the hybrid phage/polymer complex followed by the addition of GCV led to complete eradication of cancer cells in vitro.

Furthermore, not all cationic transfection reagents increase gene transfer to the same extent. It is clear that the cationic polymer, PEI, as well as CaPi result in the highest increase followed by the cationic lipid-based reagents. Based on these results (Example 6) and taking into consideration the price of lipid-based reagents, it seems that this method is not preferable.

PEI and CaPi were selected for subsequent studies to determine the underlining mechanisms of transduction mediated by chemically modified AAVP vectors. It has been reported that the complexation of adenovirus, retrovirus and AAV with cationic polymers improves transduction efficiency due to increased cellular adsorption and uptake in some cell types that are resistant to infection due to the lack of specific virus receptors. Furthermore, transduction efficiency of these viral vectors was increased by incorporation of the virus with calcium phosphate (CaPi) to form coprecipitates. These studies showed that the CaPi precipitates increase virus binding and uptake by cells. Similarly, the inventors have shown that the transduction efficiency of AAVP vectors was increased due to enhanced cell surface adsorption and cellular entry provided by the cationic polymers and CaPi coprecipitation.

These results suggest that the enhanced AAVP-mediated transduction efficiency is not only caused by the attractive interactions between the phage and the cell membrane but also by the high buffering capacity of PEI which may assist AAVP particles to escape from endosome. Previously, it has been shown that PEI has the potential to cause endosomal escape due to this buffering capacity of the endosome, caused by the presence of free amine groups present in the molecule.

Interestingly, the inventors demonstrated that the two capsid modification of AAVP vector, including the insertion of targeting ligand into coat protein to induce receptor-mediated endocytosis as well as the incorporation of cationic polymer to enhance cell adherent further improves the transduction efficiency. In this study, use of the cationic polymer PEI-complexed AAVP vectors displaying RGD4C provides the highest efficacy for AAVP-mediated transduction in $\alpha_v$ integrin-expressing cell lines.

REFERENCES

[1] L. Salimzadeh, M. Jaberipour, A. Hosseini, A. Ghaderi, Non-viral transfection methods optimized for gene delivery to a lung cancer cell line, Avicenna J Med Biotechnol, 5 (2013) 68-77.

[2] R. Waehler, S. J. Russell, D. T. Curiel, Engineering targeted viral vectors for gene therapy, Nature reviews. Genetics, 8 (2007) 573-587.

[3] S. Daya, K. I. Berns, Gene therapy using adeno-associated virus vectors, Clinical microbiology reviews, 21 (2008) 583-593.

[4] X. ZengHui, Z. XiuMei, S. WenFang, Q. QiJun, Capsid modification of adeno-associated virus and tumor targeting gene therapy, Chinese Science Bulletin, 53 (2008) 3790-3797.

[5] Y. Seow, M. J. Wood, Biological gene delivery vehicles: beyond viral vectors, Molecular therapy: the journal of the American Society of Gene Therapy, 17 (2009) 767-777.

[6] D. Bouard, D. Alazard-Dany, F. L. Cosset, Viral vectors: from virology to transgene expression, British journal of pharmacology, 157 (2009) 153-165.

[7] S. L. Hart, A. M. Knight, R. P. Harbottle, A. Mistry, H. D. Hunger, D. F. Cutler, R. Williamson, C. Coutelle, Cell binding and internalization by filamentous phage displaying a cyclic Arg-Gly-Asp-containing peptide, J Biol Chem, 269 (1994) 12468-12474.

[8] D. Larocca, A. Witte, W. Johnson, G. F. Pierce, A. Baird, Targeting bacteriophage to mammalian cell surface receptors for gene delivery, Human gene therapy, 9 (1998) 2393-2399.

[9] D. Greenstein, R. Brent, Introduction to vectors derived from filamentous phages, Curr Protoc Mol Biol, Chapter 1 (2001) Unit1 14.

[10] V. Petrenko, Evolution of phage display: from bioactive peptides to bioselective nanomaterials, Expert opinion on drug delivery, 5 (2008) 825-836.

[11] A. Hajitou, R. Rangel, M. Trepel, S. Soghomonyan, J. G. Gelovani, M. M. Alauddin, R. Pasqualini, W. Arap, Design and construction of targeted AAVP vectors for mammalian cell transduction, Nat Protoc, 2 (2007) 523-531.

[12] A. Hajitou, M. Trepel, C. E. Lilley, S. Soghomonyan, M. M. Alauddin, F. C. Marini, 3rd, B. H. Restel, M. G. Ozawa, C. A. Moya, R. Rangel, Y. Sun, K. Zaoui, M. Schmidt, C. von Kalle, M. D. Weitzman, J. G. Gelovani, R. Pasqualini, W. Arap, A hybrid vector for ligand-directed tumor targeting and molecular imaging, Cell, 125 (2006) 385-398.

[13] E. Ruoslahti, S. N. Bhatia, M. J. Sailor, Targeting of drugs and nanoparticles to tumors, The Journal of cell biology, 188 (2010) 759-768.

[14] C. A. Stoneham, M. Hollinshead, A. Hajitou, Clathrin-mediated endocytosis and subsequent endo-lysosomal trafficking of adeno-associated virus/phage, J Biol Chem, 287 (2012) 35849-35859.

[15] A. E. Nel, L. Madler, D. Velegol, T. Xia, E. M. Hoek, P. Somasundaran, F. Klaessig, V. Castranova, M. Thompson, Understanding biophysicochemical interactions at the nano-bio interface, Nat Mater, 8 (2009) 543-557.

[16] Y. Ping, C. Liu, G. Tang, J. Li, W. Yang, F. Xu, Functionalization of Chitosan via Atom Transfer Radical Polymerization for Gene Delivery, Advanced Functional Materials, 20 (2010) 3106-3116.

[17] A. Kia, J. M. Przystal, N. Nianiaris, N. D. Mazarakis, P. J. Mintz, A. Hajitou, Dual systemic tumor targeting with ligand-directed phage and Grp78 promoter induces tumor regression, Mol Cancer Ther, 11 (2012) 2566-2577.

[18] J. M. Przystal, E. Umukoro, C. A. Stoneham, T. Yata, K. O'Neill, N. Syed, A. Hajitou, Proteasome inhibition in cancer is associated with enhanced tumor targeting by the adeno-associated virus/phage, Molecular oncology, 7 (2013) 55-66.

[19] A. Hajitou, Targeted systemic gene therapy and molecular imaging of cancer contribution of the vascular-targeted AAVP vector, Adv Genet, 69 (2010) 65-82.

[20] J. M. Chilton, J. M. Le Doux, Complexation of retroviruses with polymers significantly increases the number of genes transferred to murine embryonic stem cells, but does not raise transgene expression levels, Biotechnology and applied biochemistry, 51 (2008) 141-151.

[21] A. Fasbender, J. Zabner, M. Chillon, T. O. Moninger, A. P. Puga, B. L. Davidson, M. J. Welsh, Complexes of adenovirus with polycationic polymers and cationic lipids increase the efficiency of gene transfer in vitro and in vivo, J Biol Chem, 272 (1997) 6479-6489.

[22] P. Y. Hsu, Y. W. Yang, Effect of polyethylenimine on recombinant adeno-associated virus mediated insulin gene therapy, J Gene Med, 7 (2005) 1311-1321.

[23] N. Landazuri, D. Krishna, M. Gupta, J. M. Le Doux, Retrovirus-polymer complexes: study of the factors affecting the dose response of transduction, Biotechnology progress, 23 (2007) 480-487.
[24] J. H. Lee, J. Zabner, M. J. Welsh, Delivery of an adenovirus vector in a calcium phosphate coprecipitate enhances the therapeutic index of gene transfer to airway epithelia, Hum Gene Ther, 10 (1999) 603-613.
[25] F. J. Morling, S. J. Russell, Enhanced transduction efficiency of retroviral vectors coprecipitated with calcium phosphate, Gene Ther, 2 (1995) 504-508.
[26] T. Sakoda, N. Kasahara, L. Kedes, M. Ohyanagi, Calcium phosphate coprecipitation greatly enhances transduction of cardiac myocytes and vascular smooth muscle cells by lentivirus vectors, Exp Clin Cardiol, 12 (2007) 133-138.
[27] R. W. Walters, D. Duan, J. F. Engelhardt, M. J. Welsh, Incorporation of adeno-associated virus in a calcium phosphate coprecipitate improves gene transfer to airway epithelia in vitro and in vivo, J Virol, 74 (2000) 535-540.
[28] Y. W. Yang, C. K. Chao, Incorporation of calcium phosphate enhances recombinant adeno-associated virus-mediated gene therapy in diabetic mice, J Gene Med, 5 (2003) 417-424.

The invention claimed is:

1. A method of delivering a transgene to a mammalian cell, comprising:
administering to a mammalian cell a targeted bacteriophage-polymer complex comprising a recombinant negatively charged targeted-bacteriophage and a cationic polymer selected from the group consisting of poly-D-lysine (PDL), diethylaminoethyl-dextran (DEAE.DEX) and polyethyleneimine (PEI), wherein the recombinant bacteriophage comprises a nucleic acid sequence, which encodes a protein ligand that is capable of being expressed on the capsid coat of the recombinant bacteriophage, and which is specific for a protein expressed on a mammalian target cell or tissue, so as to enable targeted delivery thereto, wherein the complex has a net positive charge and a ζ-potential of at least 5 mV at physiological pH, and wherein the complex comprises a weight: weight ratio of about 100 ng to 400 ng polymer:1 µg phage.

2. The method of claim 1, wherein the bacteriophage comprises a transgene, which exerts a therapeutic effect on a target cell, wherein the transgene comprises the Herpes simplex virus tyrosine kinase gene.

3. The method of claim 1, wherein the ligand comprises the RGD4C ligand.

4. The method of claim 1, wherein the bacteriophage is F1, Fd or M13.

5. The method of claim 1, wherein the cationic polymer comprises DEAE.DEX.

6. The method of claim 1, wherein the polymer comprises PDL.

7. The method of claim 1, wherein the complex comprises a weight:weight ratio of about 130 ng-320 ng polymer:1 µg phage.

8. The method of claim 1, wherein the bacteriophage-cationic polymer complex comprises calcium phosphate.

9. The method of claim 1, wherein the ζ-potential of the bacteriophage-polymer complex is at least 10 mV or 15 mV at physiological pH.

10. A method of delivering a transgene to a mammalian cell, comprising:
administering to a mammalian cell an aggregate comprising a plurality of bacteriophage-polymer complexes comprising a recombinant negatively charged targeted-bacteriophage and a cationic polymer selected from the group consisting of poly D-lysine (PDL), diethylaminoethyl-dextran (DEAE.DEX) and polyethyleneimine (PEI), wherein the recombinant bacteriophage comprises a nucleic acid sequence, which encodes a protein ligand that is capable of being expressed on the capsid coat of the recombinant bacteriophage, and which is specific for a protein expressed on a mammalian target cell or tissue, so as to enable targeted delivery thereto, wherein the complex has a net positive charge and a ζ-potential of at least 5 mV at physiological pH, and wherein the complex comprises a weight:weight ratio of about 100 ng to 400 ng polymer:1 µg phage.

11. The method of claim 10, wherein the mean particle size of the aggregate is between about 600 nm and 2500 nm, or between about 600 nm and 1500 nm, or between about 700 nm and 1200 nm.

12. A targeted bacteriophage-polymer complex comprising a recombinant negatively charged targeted-bacteriophage and a cationic polymer selected from the group consisting of poly-D-lysine (PDL), diethylaminoethyl-dextran (DEAE.DEX) and polyethyleneimine (PEI), wherein the recombinant bacteriophage comprises a nucleic acid sequence, which encodes a protein ligand that is capable of being expressed on the capsid coat of the recombinant bacteriophage, and which is specific for a protein expressed on a mammalian target cell or tissue, so as to enable targeted delivery thereto, wherein the complex has a net positive charge and a ζ-potential of at least 5 mV at physiological pH, and wherein the complex comprises a weight: weight ratio of about 100 ng to 400 ng polymer:1 µg phage.

13. A method of treating, preventing or ameliorating a disease in a subject using a gene therapy technique, the method comprising administering, to a subject in need of such treatment, a therapeutically effective amount of the targeted bacteriophage-polymer complex according to claim 12, or an aggregate comprising a plurality of bacteriophage-polymer complexes according to claim 12.

14. A method of producing a targeted bacteriophage-polymer complex of claim 12, comprising:
  contacting a recombinant targeted-bacteriophage with a cationic polymer to form a stable complex, which has a net positive charge.

15. The method of claim 14, wherein the bacteriophage is incubated with the cationic polymer at a temperature of about 15-30° C., or about 18-25° C., or preferably about 20-23° C., for at least 5 mins, 10 mins or 15 mins.

16. A vaccine comprising the bacteriophage-polymer complex according to claim 12, and optionally an adjuvant.

17. A genetic-molecular imaging technique comprising use of the bacteriophage-polymer complex according to claim 12, wherein the technique comprises delivering the bacteriophage-polymer complex of claim 12 to a target cell, and imaging the target cell using a molecular imaging technique.

18. A pharmaceutical composition comprising the bacteriophage-polymer complex according to claim 12, and a pharmaceutically acceptable vehicle.

* * * * *